United States Patent
Hegde

(10) Patent No.: US 10,238,642 B2
(45) Date of Patent: Mar. 26, 2019

(54) METHODS FOR TREATING NEUROGENIC ORTHOSTATIC HYPOTENSION

(71) Applicant: Theravance Biopharma R&D IP, LLC, South San Francisco, CA (US)

(72) Inventor: Sharathchandra S. Hegde, Cupertino, CA (US)

(73) Assignee: THERAVANCE BIOPHARMA R&D IP, LLC, South San Francisco, CA (US)

(*) Notice: Subject to any disclaimer, the term of this patent is extended or adjusted under 35 U.S.C. 154(b) by 0 days.

(21) Appl. No.: 15/685,119

(22) Filed: Aug. 24, 2017

(65) Prior Publication Data

US 2018/0055831 A1 Mar. 1, 2018

Related U.S. Application Data

(60) Provisional application No. 62/381,114, filed on Aug. 30, 2016.

(51) Int. Cl.
| | |
|---|---|
| *A61K 45/06* | (2006.01) |
| *A61K 31/165* | (2006.01) |
| *A61K 31/198* | (2006.01) |
| *A61K 31/573* | (2006.01) |
| *C07D 211/22* | (2006.01) |
| *A61K 31/4425* | (2006.01) |
| *A61K 31/4465* | (2006.01) |

(52) U.S. Cl.
CPC ........ *A61K 31/4465* (2013.01); *A61K 31/165* (2013.01); *A61K 31/198* (2013.01); *A61K 31/4425* (2013.01); *A61K 31/573* (2013.01); *A61K 45/06* (2013.01); *C07D 211/22* (2013.01)

(58) Field of Classification Search
CPC .... A61K 45/06; A61K 31/165; A61K 31/198; A61K 31/573; A61K 31/4425; A61K 31/4465; C07D 21/22
See application file for complete search history.

(56) References Cited

U.S. PATENT DOCUMENTS

| | | | |
|---|---|---|---|
| 4,330,558 A | 5/1982 | Suzuki et al. | |
| 6,365,632 B1 | 4/2002 | Mendel et al. | |
| 8,247,433 B2 | 8/2012 | Stangeland et al. | |
| 8,304,432 B2 | 11/2012 | Patterson et al. | |
| 8,304,433 B2 | 11/2012 | Patterson et al. | |
| 8,592,596 B2 | 11/2013 | Patterson et al. | |
| 8,604,058 B2 | 12/2013 | Patterson et al. | |
| 8,802,857 B2 | 8/2014 | Stangeland et al. | |
| 9,073,859 B2 | 7/2015 | Patterson et al. | |
| 9,162,982 B2 | 10/2015 | Patterson et al. | |
| 9,187,423 B2 | 11/2015 | Stangeland et al. | |
| 9,675,599 B2 | 6/2017 | Patterson et al. | |
| 2008/0227830 A1 | 9/2008 | Roberts et al. | |
| 2010/0125092 A1* | 5/2010 | Patterson | C07D 211/22 514/317 |
| 2013/0116286 A1 | 5/2013 | Roberts et al. | |
| 2013/0197090 A1 | 8/2013 | Hewitt et al. | |

FOREIGN PATENT DOCUMENTS

| | | |
|---|---|---|
| WO | 2010/056938 A1 | 5/2010 |
| WO | 2010056939 A1 | 5/2010 |
| WO | 2010056941 A1 | 5/2010 |

OTHER PUBLICATIONS

Isaacson et al. (Vascular Health and Risk Management (2014):10; 169-176) and Low et al. (Lancet Neurol. 2008; 7(5):451-458).*
Low et al. (Lancet Neurol. 2008; 7(5):451-458).*
Lahrmann et al. European Journal of Neurology 2006, 13: 930-936.*
Onrot et al. Neurology (1987); 37(2) Abstract Only.*
International Search Report and Written Opinion for PCT/US2017/048324 dated Oct. 25, 2017.
Altamimi, A., "The struggle of treating orthostatic hypotension with supine hypertension", Poster Abstracts, JAMDA 17, B7-B8 (2016).
Arbique et al., "Management of neurogenic orthostatic hypotension", JAMDA 15, 234-239 (2014).
Baldwin et al., "TD-9855, a novel norepinephrine and serotonin reuptake inhibitor (NSRI), demonstrates significantly reduced dependence on CYP2D6 metabolism relative to atomoxetine", Abstract No. AAPS2013-000666 (W4278) (2013).
Biaggioni, I., "New developments in the management of neurogenic orthostatic hypotension", Curr Cardiol Rep, 16(542), 1-8 (2014).
Biaggioni, I., "The pharmacology of autonomic failure: from hypotension to hypertension", Pharmacological Rev, 69:53-62 (Jan. 2017).
Figueroa et al., "Preventing and treating orthostatic hypotension: as easy as A, B, C", Cleve Clin J Med, 77(5): 298-306 (May 2010).
Goldstein et al., "Patterns of plasma levels of catechols in neurogenic orthostatic hypotension", Ann Neurol, 26:558-563 (1989).
Isaacson et al., "Neurogenic orthostatic hypotension in Parkinson's Disease: evaluation, management, and emerging role of droxidopa", Vascular Health and Risk Management, 10:169-176 (2014).
Jones et al., "Orthostatic hypotension: managing a difficult problem", Expert Review of Cardiovascular Therapy, 13(11):1263-1276 (2015).
Jordan et al., "Multiple system atrophy: using clinical pharmacology to reveal pathophysiology", Clin Auton Res, 25:53-59 (2015).
Kaufmann et al., "Norepinephrine precursor therapy in neurogenic orthostatic hypotension", Circulation, 108:724-728 (2003).
Kaufmann, H., "The orthostatic hypotension questionnaire (OHQ): a new therapy for neurogenic orthostatic hypotension", Clin Auton Res, 18[Suppl 1]:19-24 (2008).
Kaufmann, et al., "L-dihydroxyphenylserine (Droxidopa): validation of a novel symptom assessment scale", Clin Auton Res, 22:79-90 (2012).
Kuritzky et al., "Diagnosing and treating neurogenic orthostatic hypotension in primary care", Postgraduate Medicine, 127(7): 702-715 (2015).

(Continued)

*Primary Examiner* — Shirley V Gembeh
(74) *Attorney, Agent, or Firm* — Jeffrey A. Hagenah

(57) ABSTRACT

The invention relates to methods for treating neurogenic orthostatic hypotension and symptoms thereof using 4-[2-(2,4,6-trifluorophenoxymethyl)phenyl]piperidine or a pharmaceutically-acceptable salt thereof.

24 Claims, No Drawings

(56) References Cited

OTHER PUBLICATIONS

Loavenbruck et al., "Neurogenic orthostatic hypotension: roles of norepinephrine deficiency in its causes, its treatment, and future research directions", Current Medical Research & Opinion, 31(11): 2095-2104 (2015).
Low et al., "Orthostatic hypotension: mechanisms, causes, management", J Clin Neural, 11(3): 220-226 (2015).
Low et al., "Update on management of neurogenic orthostatic hypotension", Lancet Neural, 7(5): 451-458 (May 2008).
"Consensus statement on the definition of orthostatic hypotension, pure autonomic failure, and multiple system atrophy", Neurology, 46: 1470 (1996).
Northera (Droxidopa) Prescribing Information, US (Aug. 2014).
Okamoto et al., "Synergistic effect of norepinephrine transporter blockade and alpha-2 antagonism on blood pressure in autonomic failure", Hypertension, 59(3): 650-656 (Mar. 2012).
Prusiner et al., "Evidence for alpha-synuclein prions causing multiple system atrophy in humans with parkinsonism", PNAS, E5308-E5317 (2015).
Ramirez et al., "Efficacy of atomoxetine versus midodrine for the treatment of orthostatic hypotension in autonomic failure", Hypertension, 64: 1235-1240 (2014).
Ring et al., "Identification of the human cytochromes P450 responsible for atomoxetine metabolism", Drug Metabolism and Disposition, 30(3): 319-323 (2002).
Shibao et al., "Norepinephrine transporter blockade with atomoxetine induces hypertension in patients with impaired autonomic function", Hypertension, 50: 47-53 (2007).
Smith et al., "Preclinical to clinical translation of CNS transporter occupancy of TD-9855, a novel norepinephrine and serotonin reuptake inhibitor", International Journal of Neuropsychopharmacology, 1-11 (2015).
TBPH Investor Presentation (Sep. 2015).
TD-9855 phase 2 in neurogenic orthostatic hypotension (nOH), Full Text View, ClinicalTrials.gov.
Vijayan et al., "Neurogenic orthostatic hypotension—management update and role of droxidopa", Therapeutics and Clinical Risk Management, 11: 915-923 (2015).
Sanchez-Ferro et al., "The management of orthostatic hypotension in Parkinson's disease", Frontiers in Neurology, 4(64): 1-11 (Jun. 2013).
Theravance Biopharma Press Release_Aug. 1, 2018.

\* cited by examiner

METHODS FOR TREATING NEUROGENIC ORTHOSTATIC HYPOTENSION

CROSS-REFERENCE TO RELATED APPLICATIONS

This application claims the benefit of U.S. Provisional Application No. 62/381,114, filed on Aug. 30, 2016; the entire disclosure of which is incorporated herein by reference in its entirety.

BACKGROUND OF THE INVENTION

Field of the Invention

The present invention relates to methods for treating neurogenic orthostatic hypotension and the symptoms thereof using 4-[2-(2,4,6-trifluorophenoxymethyl)phenyl]-piperidine or a pharmaceutically-acceptable salt thereof.

State of the Art

Orthostatic hypotension (OH), also known as postural hypotension, is a form of low blood pressure which occurs when a person stands up. In medical terms, OH is defined as a fall in systolic blood pressure of at least 20 mm Hg or diastolic blood pressure of at least 10 mm Hg within three minutes of a postural change from supine to upright position (*Neurology* 1996; 46:1470). OH can produce a wide variety of symptoms including dizziness, lightheadedness and syncope (fainting). Due to these symptoms, OH often curtails or even prevents daily activities that require standing or walking. Additionally, OH is associated with increased morbidity and mortality. See, for example, Jones et al, *Expert Review of Cardiovascular Therapy*, 2015; 13:11, 1263-1276; Kuritzky et al., *Postgrad. Med.* 2015; 127(7):702-715; and Low et al, *J. Clin. Neurol.*, 2015; 11(3):220-226.

The underlying causes of OH can be broadly divided into neurogenic and non-neurogenic categories. Neurogenic orthostatic hypotension (nOH) is a form of OH involving the nervous system, e.g., OH caused by a peripheral or central neurologic disorder, such as primary autonomic failure (including pure autonomic failure, multiple system atrophy, and Parkinson's disease), and autonomic neuropathy (dysautonomia) (including diabetic and nondiabetic autonomic neuropathy) (Arbique et al., *JAMDA* 15 (2014) 234-239). Such disorders can cause a deficiency or dysregulation of norepinephrine which is the primary neurotransmitter that regulates blood pressure in response to postural changes (Loavenbruck et al, *Curr. Med. Res. Opin.*, 2015; 31:2095-2104). As a result, the autonomic nervous system fails to properly regulate blood pressure during a postural change and the patient experiences a significant fall in blood pressure resulting in, e.g., dizziness, lightheadedness, or syncope.

Accordingly, one objective of nOH treatment is to increase levels of norepinephrine in patients. One way to increase norepinephrine levels is to administer an agent that generates norepinephrine. For example, droxidopa (L-threo-3-4-dihydroxyphenylserine) is an amino acid that is converted by decarboxylation into norepinephrine in both the central and the peripheral nervous systems thereby increasing levels of norepinephrine (Kaufmann et al., *Circulation*, 2003; 108:724-728; Kaufmann, *Clin. Auton. Res.* (2008) 18[Suppl 1]:19-24); and Isaacson et al., *Vascular Health and Risk Management*, 2014, 10:169-176). Droxidopa is approved in the U.S. for the treatment of orthostatic dizziness, light-headedness, or the "feeling that you are about to black out" in adult patients with symptomatic nOH caused by primary autonomic failure (Parkinson's disease, multiple system atrophy, and pure autonomic failure), dopamine beta-hydroxylase deficiency, and nondiabetic autonomic neuropathy. The main side effect of droxidopa is supine hypertension and there is a black box warning in the prescribing information for this medication due to this serious side effect.

Alternatively, norepinephrine levels can be increased in patients by inhibiting the norepinephrine transporter which is responsible for norepinephrine reuptake. For example, atomoxetine is a selective norepinephrine reuptake inhibitor approved in the U.S. for treatment of attention-deficit hyperactivity disorder (ADHD). Atomoxetine has been shown to increase blood pressure in patients with central autonomic failure (Ramirez et al., *Hypertension*, 2014; 64:1235-40; and Shibao et al., *Hypertension*, 2007; 50:47-53). Atomoxetine, however, is metabolized primarily through the CYP2D6 enzymatic pathway and therefore, its pharmacokinetic properties are variable depending on whether the subject has reduced CYP2D6 activity (poor metabolizer) or normal CYP2D6 activity (extensive metabolizer) (Ring et al., *Drug Metabolism and Distribution*, 2002, 30:319-323). The prescribing information for atomoxetine also includes a number of warnings about possible drug-drug interactions. Additionally, when used to treat ADHD, atomoxetine is associated with a number of gastrointestinal adverse effects including dry mouth and nausea. Atomoxetine has not been approved for the treatment of nOH.

Other agents used to treat nOH include the α1-adrenoceptor agonist, midodrine (and its active metabolite, desglymidodrine); the synthetic mineralocortioid, fludrocortisone; and the cholinesterase inhibitor, pyridostigmine. The side effects of these agents can include, for midodrine, supine hypertension, paraesthesias (including scalp-tingling), piloerection (goose bumps), and urinary urgency or retention; for fludrocortisone, hypokalemia, headaches, peripheral edema, heart failure and supine hypertension; and for pyridostigmine, abdominal discomfort and urinary urgency.

Accordingly, it would be desirable to have other options available for treating nOH. In particular, it would be desirable to provide a safe and well-tolerated norepinephrine transporter inhibitor with predictable pharmacokinetic properties for use in the treatment of nOH. Moreover, since supine hypertension is common in nOH patients and many of the existing medications may cause or exacerbate supine hypertension, it would be highly desirable to provide compounds for treating nOH that do not cause or exacerbate supine hypertension.

U.S. Pat. No. 8,304,432 B2 and U.S. Pat. No. 8,604,058 B2 disclose 4-[2-(2-fluorophenoxymethyl)phenyl]piperidine compounds that are serotonin and norepinephrine reuptake inhibitors. A specific compound disclosed in these patents is 4-[2-(2,4,6-trifluorophenoxymethyl)phenyl]piperidine having the formula:

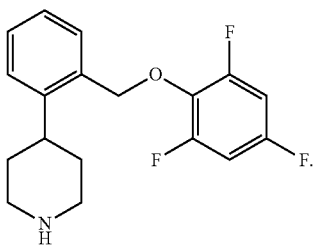 [SMILES: Fc1cc(F)c(OCc2ccccc2C2CCNCC2)c(F)c1]

This compound is also known as TD-9855. Additionally, U.S. Pat. No. 8,304,433 B2 and U.S. Pat. No. 9,073,859 B2 disclose a crystalline hydrochloride salt of 4-[2-(2,4,6-trifluorophenoxymethyl)phenyl]piperidine. These patents disclose various uses for 4-[2-(2,4,6-trifluorophenoxymethyl)phenyl]piperidine, including treatment of pain disorders, depressive disorders, cognitive disorders, stress urinary incontinence, chronic fatigue syndrome, obesity, vasomotor symptoms associated with menopause, chronic low back pain, osteoarthritis and others disorders. These patents do not disclose use of 4-[2-(2,4,6-trifluorophenoxymethyl)phenyl]piperidine for the treatment of nOH; however, information relating to a Phase 2 trial for TD-9855 in nOH was published on ClinicalTrials.gov on Mar. 9, 2016.

SUMMARY OF THE INVENTION

The present invention relates to methods for treating neurogenic orthostatic hypotension and the symptoms thereof using 4-[2-(2,4,6-trifluorophenoxymethyl)phenyl]-piperidine or a pharmaceutically-acceptable salt thereof.

Accordingly, in one aspect, the present invention relates to a method for treating neurogenic orthostatic hypotension and the symptoms thereof in a human patient, the method comprising administering to the patient a compound of formula I:

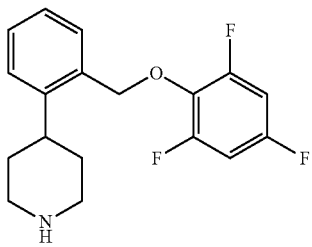

or a pharmaceutically-acceptable salt thereof. In one embodiment, administration of the compound to the patient results in one or more of: (a) an increase in the patient's seated systolic blood pressure; (b) an increase in the patient's standing time; and/or (c) a decrease in dizziness or lightheadedness experienced by the patient. In one embodiment, administration of the compound to the patient increases the patient's seated systolic blood pressure. In another embodiment, administration of the compound to the patient increases the patient's standing time. In another embodiment, administration of the compound to the patient decreases dizziness or lightheadedness experienced by the patient.

In another aspect, the present invention relates to a method for increasing seated systolic blood pressure in a human patient having symptomatic neurogenic orthostatic hypotension, the method comprising administering to the patient a compound of formula I or a pharmaceutically-acceptable salt thereof.

In another aspect, the present invention relates to a method for increasing standing time in a human patient having symptomatic neurogenic orthostatic hypotension, the method comprising administering to the patient a compound of formula I or a pharmaceutically-acceptable salt thereof.

In another aspect, the present invention relates to a method for treating orthostatic dizziness or lightheadedness in a human patient caused by symptomatic neurogenic orthostatic hypotension, the method comprising administering to the patient a compound of formula I or a pharmaceutically-acceptable salt thereof.

In another aspect, the present invention relates to a method for treating neurogenic orthostatic hypotension and the symptoms thereof in a human patient, the method comprising administering to the patient a pharmaceutical composition comprising a pharmaceutically-acceptable carrier and a compound of formula I or a pharmaceutically-acceptable salt thereof. In one embodiment, administration of the pharmaceutical composition to the patient results in one or more of (a) an increase in the patient's seated systolic blood pressure; (b) an increase in the patient's standing time; and/or (c) a decrease in dizziness or lightheadedness experienced by the patient.

In another aspect, the present invention relates to a compound of formula I or a pharmaceutically-acceptable salt thereof for use in the treatment of neurogenic orthostatic hypotension in a human patient; wherein the compound is administered to the patient in an amount ranging from about 1 mg/day to about 20 mg/day and wherein the use is characterized by (a) an increase in the patient's seated systolic blood pressure; (b) an increase in the patient's standing time; or (c) a decrease in dizziness or lightheadedness experienced by the patient.

In another aspect, the present invention relates to use of a compound of formula I or a pharmaceutically-acceptable salt thereof for the manufacture of a medicament for the treatment of neurogenic orthostatic hypotension in a human patient; wherein the compound is administered to the patient in an amount ranging from about 1 mg/day to about 20 mg/day and wherein the use is characterized by (a) an increase in the patient's seated systolic blood pressure; (b) an increase in the patient's standing time; or (c) a decrease in dizziness or lightheadedness experienced by the patient.

In another aspect, the present invention relates to a method for treating neurogenic orthostatic hypotension in a human patient, the method comprising administering to the patient a compound of formula I or a pharmaceutically-acceptable salt thereof; wherein the compound is administered to the patient in an amount ranging from about 1 mg/day to about 20 mg/day and wherein the method is characterized by (a) an increase in the patient's seated systolic blood pressure; (b) an increase in the patient's standing time; or (c) a decrease in dizziness or lightheadedness experienced by the patient.

Unless otherwise indicated, the following separate and distinct embodiments are applicable for each and every aspect of the invention described herein.

In one embodiment, the compound is 4-[2-(2,4,6-trifluorophenoxy-methyl)phenyl]piperidine hydrochloride.

In one embodiment, the compound is a crystalline hydrochloride salt of 4-[2-(2,4,6-trifluorophenoxymethyl)phenyl]piperidine characterized by a powder x-ray diffraction pattern comprising diffraction peaks at 2θ values of 4.44±0.20, 10.22±0.20, 17.16±0.20 and 21.78±0.20. In another embodiment, the crystalline hydrochloride salt of 4-[2-(2,4,6-trifluorophenoxymethyl)phenyl]piperidine is further characterized by having one or more additional diffraction peaks at 2θ values selected from 8.11±0.20, 13.18±0.20, 16.06±0.20, 18.38±0.20, 23.76±0.20, 26.32±0.20, 27.24±0.20, 29.60±0.20 and 31.94±0.20.

In one embodiment, the compound is a crystalline hydrochloride salt of 4-[2-(2,4,6-trifluorophenoxymethyl)phenyl]piperidine characterized by a differential scanning calorimetry trace having a melting point of about 197±2° C.

In one embodiment, the patient has a neurological disorder selected from primary autonomic failure (including pure autonomic failure, multiple system atrophy, and Parkinson's disease); autonomic neuropathy (including diabetic and non-diabetic autonomic neuropathy). In one embodiment, the patient has primary autonomic failure.

In another embodiment, the patient has autonomic neuropathy. In another embodiment, the patient has Parkinson's disease. In a particular embodiment, the patient has multiple system atrophy.

In one embodiment, the compound is administered in an amount ranging from about 0.5 mg/day to about 20 mg/day. In another embodiment, the compound is administered in an amount ranging from about 1 mg/day to about 20 mg/day. In another embodiment, the compound is administered in an amount ranging from about 1 mg/day to about 10 mg/day. In another embodiment, the compound is administered in an amount selected from about 1, 2, 3, 4, 5, 6, 7, 8, 9 and 10 mg/day.

In one embodiment, the compound is administered once per day.

In one embodiment, the compound is administered as a pharmaceutical composition comprising a pharmaceutically-acceptable carrier and a compound of formula I or a pharmaceutically-acceptable salt thereof.

In one embodiment, the compound is administered with an agent selected from an al-adrenoceptor agonist, an α-2 adrenergic receptor antagonist, a corticosteroid, a norepinephrine precursor and a cholinesterase inhibitor; or a combination thereof. In a particular embodiment, the compound is administered with midodrine, fludrocortisone acetate, droxidopa or pyridostigmine, or, in each case, a pharmaceutically-acceptable salt thereof; such as midodrine hydrochloride or pyridostigmine bromide.

Other aspects and embodiments of this invention are disclosed herein.

DETAILED DESCRIPTION OF THE INVENTION

In its various aspects and embodiments, the present invention relates to methods for treating neurogenic orthostatic hypotension and the symptoms thereof using 4-[2-(2,4,6-trifluorophenoxymethyl)phenyl]piperidine (the compound of formula I) or a pharmaceutically-acceptable salt thereof.

Definitions

When describing present invention, the following terms have the following meanings unless otherwise indicated.

The singular terms "a," "an" and "the" include the corresponding plural terms unless the context of use clearly dictates otherwise.

The term "about" means±5 percent of the specified value.

The term "melting point" means the temperature at which the maximum endothermic heat flow is observed by differential scanning calorimetry for the thermal transition that corresponds to the solid-to-liquid phase change.

The term "pharmaceutically-acceptable" means acceptable for administration to a patient (e.g., having acceptable safety for the specified usage).

The term "pharmaceutically-acceptable salt" means a salt prepared from an acid and a base (including zwitterions) that is acceptable for administration to a patient (e.g., a salt having acceptable safety for a given dosage regime).

The term "therapeutically effective amount" means an amount sufficient to effect treatment when administered to a patient in need of treatment, e.g., the amount needed to obtain the desired therapeutic effect.

The term "treating" or "treatment" means ameliorating or suppressing the medical condition or disorder being treated; or alleviating the symptoms of the medical condition or disorder.

The term "unit dosage form" or "unit doses" means a physically discrete unit suitable for dosing a patient, i.e., each unit containing a predetermined quantity of a therapeutic agent calculated to produce a therapeutic effect either alone or in combination with one or more additional units. Examples include capsules, tablets and the like.

All other terms used herein are intended to have their ordinary meaning as understood by persons having ordinary skill in the art to which they pertain.

Compound of Formula I

The present invention employs 4-[2-(2,4,6-trifluorophenoxymethyl)phenyl]-piperidine having formula I:

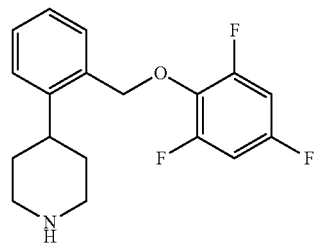

or a pharmaceutically-acceptable salt thereof.

4-[2-(2,4,6-Trifluorophenoxymethyl)phenyl]piperidine can be prepared as described in the Examples herein or by the methods and procedures disclosed in U.S. Pat. Nos. 8,304,432 B2; 8,304,433 B2; and 8,247,433 B2; and related patents.

In one embodiment, 4-[2-(2,4,6-trifluorophenoxymethyl)phenyl]piperidine is used in the form of a pharmaceutically-acceptable salt. Representative pharmaceutically-acceptable salts include salts of the following acids (with the corresponding anion shown in parentheses): acetic (acetate), ascorbic (ascorbate), benzenesulfonic (benzenesulfononate or besylate), benzoic (benzoate), camphorsulfonic (camphorsulfonate), chlortheophylline (chlortheophyllinate), citric (citrate), ethanesulfonic (ethanesulfonate), ethanedisulfonic or edisylic (ethanedisulfonate or edisylate), fumaric (fumarate), gentisic (gentisate), gluconic (gluconate), glucuronic (glucoronate), gluceptic (gluceptate), glutamic (glutamate), hippuric (hippurate), hydrobromic (bromide), hydrochloric (chloride), hydroiodic (iodide), isethionic (isethionate), lactic (lactate), lactobionic (lactobionate), laurylsulfonic (laurylsulfonate), maleic (maleate), malic (malate), mandelic (mandelate), methanesulfonic (methanesulfonate or mesylate), methyl sulfonic (methyl sulfonate), mucic (mucate), naphthalenesulfonic (naphthalenesulfonate or napsylate), naphthalene-1,5-disulfonic (naphthalene-1,5-disulfonate), naphthalene-2,6-disulfonic (naphthalene-2,6-disulfonate), naphthoic (naphthoate), nicotinic (nicotinate), nitric (nitrate), octadecanonic (octadecanoate), oleic (oleate), orotic (orotate), oxalic (oxalate), pamoic (pamoate), pantothenic (pantothenate), phosphoric (phosphate), polygalacturonic (polygalacturonate), succinic (succinate), sulfosalicylic (sulfosalicylate), sulfuric (sulfate), tartaric (tartarate), p-toluenesulfonic (p-toluenesulfonate or tosylate) and xinafoic (xinafoate) acid, and the like. Such salts are sometimes referred to as acid addition salts.

The salts can be prepared by contacting one molar equivalent of 4-[2-(2,4,6-trifluorophenoxymethyl)phenyl]piperidine with about 0.95 to about 1.05 molar equivalents of acidic protons in the pharmaceutically-acceptable acid. For example, one molar equivalent of 4-[2-(2,4,6-trifluorophenoxymethyl)phenyl]piperidine can be contacted with about one molar equivalent of hydrochloric acid to form 4-[2-(2,4,6-trifluorophenoxymethyl)phenyl]piperidine hydrochloride; or one molar equivalent of 4-[2-(2,4,6-trifluorophenoxymethyl)phenyl]piperidine can be contacted with about 0.5 molar equivalents of sulfuric acid to form 4-[2-(2,4,6-trifluorophenoxymethyl)phenyl]-piperidine sulfuric acid salt.

Such reactions are typically conducted in a diluent, such as dichloromethane, ethanol, ethyl acetate, isopropyl acetate and the like, at a temperature ranging from about −20° C. to about 50° C. for about 0.5 to about 12 hours or until the reaction is substantially complete. Upon completion of the reaction, the product is typically isolated using conventional procedures, such as filtration, chromatography, recrystallization, and the like. The product of such reactions may or may not be crystalline.

In one embodiment, the compound employed in the present invention is 4-[2-(2,4,6-trifluorophenoxymethyl)phenyl]piperidine hydrochloride. In another embodiment, the compound is crystalline 4-[2-(2,4,6-trifluorophenoxymethyl)phenyl]piperidine hydrochloride characterized by a powder x-ray characterized comprising diffraction peaks at 2θ values of 4.44±0.20, 10.22±0.20, 17.16±0.20 and 21.78±0.20. In another embodiment, the crystalline hydrochloride salt is further characterized by having one or more additional diffraction peaks at 2θ values selected from 8.11±0.20, 13.18±0.20, 16.06±0.20, 18.38±0.20, 23.76±0.20, 26.32±0.20, 27.24±0.20, 29.60±0.20 and 31.94±0.20. In another embodiment, the compound is crystalline 4-[2-(2,4,6-trifluorophenoxymethyl)phenyl]piperidine hydrochloride characterized by a differential scanning calorimetry trace having a melting point of about 197±2° C.

The crystalline hydrochloride salts of 4-[2-(2,4,6-trifluorophenoxymethyl)-phenyl]piperidine employed in this invention can be prepared as described in the Examples herein or by the methods and procedures disclosed in U.S. Pat. Nos. 8,304,432 B2; 8,304,433 B2; and 8,247,433 B2; and related patents.

Pharmaceutical Compositions, Formulations and Dosage Forms

When used in the present invention, 4-[2-(2,4,6-trifluorophenoxymethyl)phenyl]-piperidine or a pharmaceutically-acceptable salt thereof is typically administered to a patient in the form of a pharmaceutical composition or formulation. When discussing compositions or formulations herein, 4-[2-(2,4,6-trifluorophenoxymethyl)phenyl]-piperidine or a pharmaceutically-acceptable salt thereof may be referred to as the "active agent" to distinguish it from other components of the formulation such as the carrier or excipient. Thus, the term "active agent" includes 4-[2-(2,4,6-trifluorophenoxymethyl)-phenyl]piperidine as well as pharmaceutically-acceptable salts thereof. Also, the terms "carrier" and "excipient" are used interchangeably herein and have the same meaning unless otherwise indicated.

Pharmaceutical compositions of the invention typically contain a therapeutically effective amount of the active agent. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, a pharmaceutical composition will contain from about 0.01 to about 95 wt. % of active agent, including, from about 0.01 to about 30 wt. %, such as from about 0.01 to about 10 wt. %, with the actual amount depending upon the formulation, the route of administration, the frequency of dosing, and so forth. For example, a pharmaceutical composition suitable as an oral dosage form may contain about 0.1 to about 10 wt. %, including from about 0.5 to about 5 wt. %, of active agent.

In one representative embodiment, the pharmaceutical composition contains from about 0.5 to about 20 mg of active agent per unit dose, including from about 1 to about 10 mg of active agent per unit dose. For example, the active agent may be formulated in 1, 2, 3, 4, 5, 6, 7, 8, 9, or 10 mg unit doses, such as 1 mg, 3 mg, 5 mg, and 10 mg unit doses.

Any conventional or suitable pharmaceutically-acceptable carrier may be used in the pharmaceutical compositions of this invention. The choice of a particular carrier, or combinations of carriers, will depend on various factors, such as the mode of administration, dosage amount, frequency of dosing, timing of release of the active agent and the like. In this regard, the preparation of a suitable pharmaceutical composition for a particular mode of administration is well within the scope of those skilled in the pharmaceutical arts, and carriers used in such compositions are commercially available. By way of further illustration, conventional formulations and formulation techniques are described in, e.g., *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of pharmaceutically-acceptable carriers include, but are not limited to: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically-acceptable carrier and any optional ingredients. The resulting uniformly blended mixture may then be shaped or loaded into tablets, capsules, pills, canisters, cartridges, vials, bottles, dispensers, and the like, using conventional procedures and equipment.

In one embodiment, the pharmaceutical composition is suitable for oral administration. Pharmaceutical compositions for oral administration may be in the form of, for example, capsules, tablets, pills, lozenges, cachets, dragees, powders, granules, solutions, suspensions, emulsions, elixirs, syrups, and the like; each containing a predetermined amount of the active agent.

When intended for oral administration in a solid dosage form (such as capsules, tablets, and the like), the pharmaceutical composition will typically comprise the active agent and one or more pharmaceutically-acceptable solid carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as croscarmellose sodium, agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; buffering agents; release agents; coating agents; sweetening, flavoring and perfuming agents; and preservatives and antioxidants.

Representative coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, polyvinyl alcohol and the like.

Representative antioxidants include: water-soluble antioxidants, such as ascorbic acid, cysteine hydrochloride, sodium bisulfate, sodium metabisulfate, sodium sulfite, and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Pharmaceutical compositions may also be formulated to provide slow or controlled-release of the active agent using, by way of example, hydroxypropyl methyl cellulose in varying proportions or other polymer matrices, liposomes and/or microspheres. In addition, the pharmaceutical composition may contain opacifying agents and may be formulated so that they release the active agent only, or preferentially, in a certain portion of the gastrointestinal tract, optionally, in a delayed manner.

Examples of embedding compositions which can be used include polymeric substances and waxes. The active agent can also be in micro-encapsulated form, if appropriate, with one or more of the above-described excipients.

Suitable liquid dosage forms for oral administration include, by way of example, pharmaceutically-acceptable emulsions, microemulsions, solutions, suspensions, syrups and elixirs. Liquid dosage forms typically comprise the active agent and an inert diluent, such as, for example, water, juice or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In another embodiment, the pharmaceutical composition is suitable for topical administration, such as transdermal administration. For such administration, known transdermal delivery systems and excipients may be employed. For example, the active agent can be admixed with permeation enhancers, such as propylene glycol, polyethylene glycol monolaurate, azacycloalkan-2-ones, and the like, and incorporated into a patch or similar delivery system. Additional excipients, including gelling agents, emulsifiers and buffers, may be used in such transdermal compositions, if desired.

In another embodiment, the pharmaceutical composition is suitable for parenterally administration (e.g., by subcutaneous, intravenous, intramuscular, or intraperitoneal injection). For such administration, the active agent is provided in a sterile solution, suspension, or emulsion. Exemplary carriers for preparing such formulations include water, saline, low molecular weight alcohols such as propylene glycol, polyethylene glycol, oils, gelatin, fatty acid esters such as ethyl oleate, and the like. Parenteral formulations may also contain one or more solubilizers, stabilizers, preservatives, wetting agents, emulsifiers, and dispersing agents. These formulations may be rendered sterile by use of a sterile injectable medium, a sterilizing agent, filtration, irradiation, or heat.

A typical intravenous formulation is a sterile pH 4-7 aqueous solution comprising the active agent and a physiologically-acceptable aqueous carrier. Representative physiologically-acceptable aqueous carriers include, by way of example, Sterile Water for Injection, USP; Dextrose Injection, USP (e.g., 2.5, 5.0, 10, 20% dextrose, including 5% Dextrose Injection (D5/W)); Dextrose and Sodium Chloride Injection, USP (e.g., dextrose varying from 2.5 to 10% and sodium chloride varying from 0.12 (19 mEq sodium) to 0.9% (154 mEq sodium)); Mannitol Injection, USP, (e.g., 5, 10, 15, 20 and 25% mannitol); Ringer's Injection, USP (e.g., 147 mEq sodium, 4 mEq potassium, 4.5 mEq calcium and 156 mEq chloride per liter); Lactated Ringer's Injection, USP (e.g., 2.7 mEq calcium, 4 mEq potassium, 130 mEq sodium, and 28 mEq lactate per liter); Sodium Chloride Injection, USP (e.g., 0.9% sodium chloride) and the like. When administered to a patient, the active agent will typically be diluted in about 0.1 mL to about 10 mL of the aqueous carrier per mg of the active agent, such as about 0.5 to about 5 mL per mg. The dosing solution is then typically administered to the patient by intravenous infusion.

By way of illustration, representative pharmaceutical compositions can be prepared as described in the following examples.

A. Hard Gelatin Capsules

The active agent (5 g), spray-dried lactose (485 g) and magnesium stearate (10 g) are thoroughly blended. The resulting composition is then loaded into hard gelatin capsules (500 mg of composition per capsule). Each capsule provides 5 mg of the active agent per unit dose suitable for oral administration.

B. Hard Gelatin Capsules

The active agent (2 g) is thoroughly blended with starch (98 g), microcrystalline cellulose (98 g) and magnesium stearate (2 g). The mixture is then passed through a No. 45 mesh U.S. sieve and loaded into hard gelatin capsules (200 mg of composition per capsule). Each capsule provides 2 mg of the active agent per unit dose suitable for oral administration.

C. Soft Gelatin Capsules

The active agent (5 g) is thoroughly blended with polyoxyethylene sorbitan monooleate (65 g) and starch powder (335 g). The mixture is then loaded into soft gelatin capsules (400 mg of composition per capsule). Each capsule provides 5 mg of the active agent per unit dose suitable for oral administration.

D. Soft Gelatin Capsules

The active agent (1 g) is thoroughly blended with microcrystalline cellulose (290 g) and magnesium stearate (9 g). The mixture is then loaded into soft gelatin capsules (300 mg of composition per capsule). Each capsule provides 1 mg of the active agent per unit dose suitable for oral administration.

E. Tablets

The active agent (10 g), starch (45 g) and microcrystalline cellulose (35 g) are passed through a No. 20 mesh U.S. sieve and mixed thoroughly. The resulting granules are dried at 50-60° C. and passed through a No. 16 mesh U.S. sieve. Separately, a solution of polyvinylpyrrolidone (4 g as a 10% solution in sterile water) is mixed with sodium carboxymethyl starch (4.5 g), magnesium stearate (0.5 g), and talc (1 g), and this mixture is passed through a No. 16 mesh U.S. sieve. The resulting mixture is then added to the granules. After mixing thoroughly, the mixture is compressed on a tablet press to form tablets weighing 100 mg each. Each tablet provides 10 mg of the active agent per unit dose suitable for oral administration.

F. Tablets

The active agent (40 g) is thoroughly blended with microcrystalline cellulose (445 g), silicon dioxide fumed (10 g), and stearic acid (5 g). The mixture is then compressed on a tablet press to form tablets weighing 100 mg each. Each tablet provides 8 mg of the active agent per unit dose suitable for oral administration.

G. Tablets

The active agent (10 g) is thoroughly blended with cornstarch (50 g), croscarmellose sodium (25 g), lactose (110 mg), and magnesium stearate (5 mg). The mixture is then compressed on a tablet press to form tablets weighting 200 mg each. Each tablet provides 10 mg of the active agent per unit dose suitable for oral administration.

H. Tablets

The active agent (10 g) is thoroughly blended with cornstarch (230 g) and an aqueous solution of gelatin (50 g). The mixture is dried and ground to a fine powder. Microcrystalline cellulose (100 g) and magnesium stearate (10 g) are then admixed with the gelatin formulation, granulated and the resulting mixture compressed on a tablet press to form tablets weighing 200 mg each. Each tablet provides 5 mg of the active agent per unit dose suitable for oral administration.

I. Syrup

The following ingredients are thoroughly mixed until all the solid ingredients are dissolved:

| Ingredients | Amount |
| --- | --- |
| Active Agent | 0.5 g |
| Citric acid | 2.1 g |
| Artificial Raspberry Flavor | 2.0 mL |
| Methyl Paraben | 2.0 g |
| Propyl Paraben | 0.5 g |
| Sorbitol Solution USP (64% solution), to make | 1000.0 mL |

The resulting syrup contains 5 mg of active agent per 10 mL of syrup suitable for oral administration.

J. Sterile Intravenous Solution

The active agent (5 mg) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by intravenous infusion.

Co-Administration and Combinations

If desired, 4-[2-(2,4,6-trifluorophenoxymethyl)phenyl]piperidine or a pharmaceutically-acceptable salt thereof may be administered in combination with one or more other therapeutic agents ("secondary agents") to treat nOH and the symptoms thereof.

Representative classes of therapeutic agents that can be administered in combination with 4-[2-(2,4,6-trifluorophenoxymethyl)phenyl]piperidine or a pharmaceutically-acceptable salt thereof include, by way of example, $\alpha_1$-adrenergic receptor ($\alpha_1$-adrenoceptor) agonists, $\alpha_2$-adrenergic receptor ($\alpha_2$-adrenoceptor) antagonists, corticosteroids, norepinephrine precursors, cholinesterase inhibitors; or combinations thereof. Those skilled in the art will understand that the terms "$\alpha_1$-adrenergic receptor agonist," "$\alpha_2$-adrenergic receptor antagonist," "corticosteroid," "norepinephrine precursor", and "cholinesterase inhibitor" include all forms of compounds having the specified activity after administration to the patient, such as pharmaceutically-acceptable salts, solvates, crystalline forms, polymorphs, prodrugs and the like. Similarly, the term "secondary agent" includes all forms of the secondary agent, such as pharmaceutically-acceptable salts, solvates, crystalline forms, polymorphs, prodrugs and the like.

Representative examples of $\alpha_1$-adrenergic receptor agonists include desglymidodrine, etilefrine, metaraminol, midodrine and the like, or, in each case, pharmaceutically-acceptable salts thereof. Midodrine is a prodrug of desglymidodrine, which is an $\alpha_1$-adrenergic receptor agonist. In one embodiment, the secondary agent is midodrine or a pharmaceutically-acceptable salt thereof, such as midodrine hydrochloride.

Representative examples of α$_2$-adrenergic receptor antagonists include yohimbine and the like, or pharmaceutically-acceptable salts thereof.

Representative examples of corticosteroids include fludrocortisone, fludrocortisone acetate and the like, or, in each case, pharmaceutically-acceptable salts thereof. Fludrocortisone acetate is a prodrug of fludrocortisone. In one embodiment, the secondary agent is fludrocortisone acetate.

Representative examples of norepinephrine precursors include droxidopa or pharmaceutically-acceptable salts thereof. In one embodiment, the secondary agent is droxidopa.

Representative examples of cholinesterase inhibitors include pyridostigmine or a pharmaceutically-acceptable salt thereof. In one embodiment, the secondary agent is pyridostigmine or a pharmaceutically-acceptable salt thereof, such as pyridostigmine bromide.

4-[2-(2,4,6-Trifluorophenoxymethyl)phenyl]piperidine or a pharmaceutically-acceptable salt thereof and the secondary agent may be either physically mixed to form a composition containing both agents; or each agent may be administered separately to the patient, either simultaneously or sequentially. For example, 4-[2-(2,4,6-trifluorophenoxymethyl)phenyl]piperidine or a pharmaceutically-acceptable salt thereof can be combined with a secondary agent using conventional procedures and equipment to form a combination of agents comprising 4-[2-(2,4,6-trifluorophenoxymethyl)phenyl]piperidine or a pharmaceutically-acceptable salt thereof and the secondary agent. Additionally, the agents may be combined with a pharmaceutically-acceptable carrier to form a pharmaceutical composition comprising a 4-[2-(2,4,6-trifluorophenoxymethyl)phenyl]-piperidine or a pharmaceutically-acceptable salt thereof, the secondary agent and a pharmaceutically-acceptable carrier. In this embodiment, the components of the composition are typically mixed or blended to create a physical mixture. The physical mixture is then administered to the patient by any suitable route of administration, such as oral, topical or parenteral modes of administration.

Alternatively, the agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of 4-[2-(2,4,6-trifluorophenoxymethyl)phenyl]piperidine or a pharmaceutically-acceptable salt thereof, e.g., ranging anywhere from concurrent administration to about 24 hours post-dose. This is also referred to as sequential administration. Thus, for example, 4-[2-(2,4,6-trifluorophenoxymethyl)phenyl]piperidine or a pharmaceutically-acceptable salt thereof can be orally administered simultaneously or sequentially with a secondary agent using two tablets (e.g., one tablet for each active agent), where sequential includes being administered immediately before or after administration of 4-[2-(2,4,6-trifluorophenoxymethyl)phenyl]piperidine or a pharmaceutically-acceptable salt thereof or at some other time (e.g., one hour before or after; or three hours before or after, etc.). Alternatively, the combination may be administered by different routes of administration, e.g., one orally and the other topically or parenterally.

When employed in the present invention, the secondary agent is used in a therapeutically effective amount, i.e., in an amount that produces a therapeutically beneficial effect when co-administered with 4-[2-(2,4,6-trifluorophenoxymethyl)phenyl]-piperidine or a pharmaceutically-acceptable salt thereof. For example, such agents are typically employed in their approved dosage amounts. For example, midodrine hydrochloride is typically administered orally in an amount ranging from about 2.5 mg to about 10 mg up to three times per day; and droxidopa is typically administered orally in an amount ranging from about 100 mg to about 600 mg up to three times per day.

Utility

4-[2-(2,4,6-Trifluorophenoxymethyl)phenyl]piperidine is expected to be useful for the treatment of neurogenic orthostatic hypotension (nOH) and symptoms related to nOH, such as dizziness, light-headedness, or a feeling by the patient that he or she is about to black out.

4-[2-(2,4,6-Trifluorophenoxymethyl)phenyl]piperidine has various properties that may make it particularly useful for treating nOH. For example, unlike atomoxetine, metabolism of 4-[2-(2,4,6-trifluorophenoxymethyl)phenyl]piperidine is catalyzed by multiple CYP450 enzymes and therefore, no significant increases in exposure are expected in individuals with the CYP2D6 poor metabolizer (PM) phenotype (Baldwin et al., "*TD-9855, a Novel Norepinephrine and Serotonin Reuptake Inhibitor (NSRI), Demonstrates Significantly Reduced Dependence on CYP2D6 Metabolism Relative to Atomoxetine*" Poster Presented at American Association of Pharmaceutical Scientists Annual Meeting and Exposition, Poster No. W4278, San Antonio, Tex. (2013); Abstract No. AAPS2013-000666). More specifically, metabolism of 4-[2-(2,4,6-trifluorophenoxymethyl)phenyl]piperidine was minimally impacted by chemical inhibition of CYP2D6 (7% reduction) and was primarily mediated by CYP3A4 and CYP1A2 (34% and 25% reductions, respectively). In contrast, atomoxetine metabolism was significantly impacted by chemical inhibition of CYP2D6 (94% reduction) and was not significantly impacted by inhibition of other CYP450 enzymes. Thus, relative to atomoxetine, 4-[2-(2,4,6-trifluorophenoxymethyl)phenyl]piperidine is expected to have a significantly reduced potential for drug-drug interactions and reduced susceptibility to liabilities associated with CYP2D6 polymorphism.

In one embodiment, 4-[2-(2,4,6-trifluorophenoxymethyl)phenyl]piperidine or a pharmaceutically-acceptable salt thereof is used to treat symptomatic nOH caused by primary autonomic failure (including pure autonomic failure, multiple system atrophy and Parkinson's disease), or autonomic neuropathy (including diabetic and nondiabetic autonomic neuropathy).

In a particular embodiment, 4-[2-(2,4,6-trifluorophenoxymethyl)phenyl]piperidine or a pharmaceutically-acceptable salt thereof is used to treat symptomatic nOH caused by primary autonomic failure. In this embodiment, the patient may be diagnosed with pure autonomic failure, multiple system atrophy and/or Parkinson's disease. In one embodiment, the patient has pure autonomic failure. In another embodiment, the patient has multiple system atrophy. And in another embodiment, the patient has Parkinson's disease.

Primary autonomic failure (also called primary dysautonomia) is a category of dysautonomia, i.e., a condition in which the autonomic nervous system does not function properly. In primary autonomic failure, the autonomic dysfunction occurs as a primary condition as opposed to a secondary condition resulting from another disease, such as diabetes. For example, autonomic failure is typically categorized as "primary" when it results from a chronic condition characterized by degeneration of the autonomic nervous system or where autonomic failure is the predominant symptom and its cause is unknown. Conditions categorized as primary autonomic failure include pure autonomic failure, multiple system atrophy, and Parkinson's disease.

Pure autonomic failure (PAF), also known as Bradbury-Eggleston syndrome or idiopathic orthostatic hypotension, is a degenerative disease of the autonomic nervous system. A primary symptom of PAF is orthostatic hypotension. Other symptoms may include decreased sweating, heat intolerance, urinary retention, bladder spasms (possibly causing incontinence), erectile dysfunction, fecal incontinence or constipation, and pupillary abnormalities. The cause of PAF is not completely understood, but the loss of cells in the intermediolateral column of the spinal cord has been documented in patients with PAF. Additionally, PAF may be related to abnormal accumulation of alpha-synuclein.

Parkinson's disease (PD) is a chronic and progressive movement disorder. The cause is unknown, but PD involves the malfunction and death of neurons in an area of the midbrain called the substantia nigra. These neurons produce dopamine which plays a key role in movement and coordination. As PD progresses, the amount of dopamine produced in the brain decreases resulting in motor control and coordination problems. Symptoms include tremor, rigidity, slowness of movement, and postural instability. However, some PD patients also experience non-motor symptoms including orthostatic hypotension due to alterations in the autonomic nervous system, i.e., PD plus symptoms of nOH. Additionally, some patients with PD symptoms have a condition known as Parkinson-plus syndromes (or disorders of multiple system degeneration). Parkinson-plus syndromes is a group of neurodegenerative diseases that produce the classical symptoms of PD (tremor, rigidity, akinesia/bradykinesia, and postural instability) with additional features that distinguish them from simple idiopathic PD. Clinical features distinguishing Parkinson-plus syndromes from idiopathic PD include symmetrical onset, a lack of or irregular resting tremor, and a reduced response to dopaminergic drugs (including levodopa). Additional features include bradykinesia, early-onset postural instability, increased rigidity in axial muscles, dysautonomia, alien limb syndrome, supranuclear gaze palsy, apraxia, involvement of the cerebellum including the pyramidal cells, and in some instances significant cognitive impairment.

Multiple system atrophy (MSA), also known as Shy-Drager syndrome, is a progressive neurodegenerative disorder characterized by a combination of symptoms that affect both the autonomic nervous system and movement. The initial symptoms of MSA are often difficult to distinguish from the initial symptoms of Parkinson's disease and include slowness of movement, tremor, or rigidity (stiffness); clumsiness or incoordination; impaired speech, a croaky, quivering voice; fainting or lightheadedness due to orthostatic hypotension; bladder control problems, such as a sudden urge to urinate or difficulty emptying the bladder. MSA is divided into two different types depending on the most prominent symptoms at the time an individual is evaluated: the parkinsonian type (MSA-P), with primary characteristics similar to Parkinson's disease (such as moving slowly, stiffness, and tremor) along with problems of balance, coordination, and autonomic nervous system dysfunction; and the cerebellar type (MSA-C), with primary symptoms featuring ataxia (problems with balance and coordination), difficulty swallowing, speech abnormalities or a quavering voice, and abnormal eye movements. The cause of MSA is unknown. A distinguishing feature of MSA is the accumulation of the protein alpha-synuclein in glia, the cells that support nerve cells in the brain. These deposits of alpha-synuclein particularly occur in oligodendroglia, a type of cell that makes myelin (a coating on nerve cells that lets them conduct electrical signals rapidly). A recent study indicates that a prion form of the alpha-synuclein protein may be the cause of the disease (Prusiner et al, *PNAS*, (2015) 112: E5308-17).

4-[2-(2,4,6-Trifluorophenoxymethyl)phenyl]piperidine or a pharmaceutically-acceptable salt thereof is particularly useful for treating MSA because of the pharmacology of MSA. More specifically, MSA is characterized by central autonomic pathway degeneration; however, peripheral postganglionic noradrenergic fibers and catecholamine reuptake mechanisms appear to be intact in MSA patients thus maintaining sympathetic tone (Biaggioni, *Pharmacolgical Reviews* (2017) 69(1): 53-62). Normally, peripheral increases in norepinephrine concentration upon standing are counteracted by CNS sympatholytic activity mediated by norepinephrine-activated central α2-adrenoreceptors, thus buffering the peripheral pressor effect and maintaining postural normotension. In MSA, however, intact peripheral sympathetic postganglionic adrenergic fibers are essentially "disconnected" from CNS modulation thus allowing full unmasking of the norepinephrine pressor effect. Although residual sympathetic tone in these patients cannot be modulated by baroreflex pathways or CNS input due to this "disconnection," it can be targeted pharmacologically. Taking advantage of this unique pathophysiology, increasing peripheral sympathetic synaptic norepinephrine using 4-[2-(2,4,6-trifluorophenoxymethyl)phenyl]piperidine or a pharmaceutically-acceptable salt thereof should induce a pressor effect in MSA patients with nOH. Accordingly, in a particular embodiment, 4-[2-(2,4,6-trifluorophenoxymethyl)phenyl]piperidine or a pharmaceutically-acceptable salt thereof is used to treat symptomatic nOH caused by MSA.

In another particular embodiment, 4-[2-(2,4,6-trifluorophenoxymethyl)phenyl]-piperidine or a pharmaceutically-acceptable salt thereof is used to treat symptomatic nOH caused by autonomic neuropathy. Autonomic neuropathy, or dysautonomia, refers to various conditions in which the autonomic nervous system (ANS) does not work properly. Autonomic neuropathy is a type of neuropathy affecting the nerves that carry information from the brain and spinal cord to the heart, bladder, intestines, sweat glands, pupils, and blood vessels. The primary symptoms of autonomic neuropathy, which can vary between individuals, include: orthostatic hypotension; dry mouth; rapid heart rate; tunnel vision; difficulty swallowing; bowel incontinence; blurry vision; urinary incontinence; constipation; anhydrosis; and sexual disfunction. Autonomic neuropathy may be due to inherited or degenerative neurologic diseases (primary dysautonomia) or it may occur due to injury of the autonomic nervous system from an acquired disorder (secondary dysautonomia).

When used to treat nOH or the symptoms of nOH, 4-[2-(2,4,6-trifluorophenoxymethyl)phenyl]piperidine or a pharmaceutically-acceptable salt thereof is typically administered to the patient in an amount ranging from about 0.5 mg to about 20 mg per day; or as needed. In one embodiment, the amount administered to the patient ranges from about 1 mg to about 10 mg per day. In another embodiment, the amount administered to the patient ranges from about 3 mg to about 10 mg per day. In separate and distinct embodiments, the amount administered to the patient is 1, 2, 3, 4, 5, 6, 7, 8, 9, or 10 mg per day, including 1 mg, 3 mg, 5 mg, or 10 mg per day. The amount administered to the patient, the route of administration and the frequency of administration will typically be determined by the physician treating the patient.

4-[2-(2,4,6-Trifluorophenoxymethyl)phenyl]piperidine or a pharmaceutically-acceptable salt thereof may be administered to the patient by any acceptable route of administration including, for example, oral, topical (including transdermal) and parenteral (including intravenous) modes of administration.

In one embodiment, 4-[2-(2,4,6-trifluorophenoxymethyl) phenyl]piperidine or a pharmaceutically-acceptable salt thereof is administered to the patient orally in a solid or liquid dosage form. In a particular embodiment, the form administered to the patient is a solid dosage form including a tablet or capsule. In another particular embodiment, the form administered to the patient is a liquid dosage form including a solution, syrup, suspension or emulsion.

In another embodiment, the route of administration is topical. In a particular embodiment, the route of administration is transdermal using a transdermal patch.

In another embodiment, the route of administration is parenteral. In a particular embodiment, the route of administration is intravenous administration.

4-[2-(2,4,6-Trifluorophenoxymethyl)phenyl]piperidine or a pharmaceutically-acceptable salt thereof may be administered to the patient in a single daily dose (e.g., once a day); in multiple doses per day (e.g., twice, three times or four times daily); or in multiple doses per week (e.g., twice, three times, four times, five times or six times per week). Alternatively, a pharmaceutical composition may be administered continuously using, for examples, a transdermal patch. In a particular embodiment, 4-[2-(2,4,6-trifluorophenoxymethyl)phenyl]piperidine or a pharmaceutically-acceptable salt thereof is administered to the patient once per day.

EXAMPLES

The following examples are provided to illustrate various representative embodiments and aspects of this invention and are not intended to limit the scope of this invention unless specifically indicated.

All reagents, starting materials and solvents used in the following examples were purchased from commercial suppliers (such as Sigma-Aldrich, St. Louis, Mo. and its affiliates) and were used without further purification unless otherwise indicated.

The following abbreviations have the following meanings unless otherwise indicated:
AcOH acetic acid
BP blood pressure
BSA bovine serum albumin
CHO Chinese hamster ovary
DA dopamine
DAT dopamine transporter
DCM dichloromethane
DIPEA N,N-diisopropylethylamine
DMEM Dulbecco's Modified Eagle's Medium
DMF N,N-dimethylformamide
DMSO dimethyl sulfoxide
EDTA ethylenediaminetetraacetic acid
EtOAc ethyl acetate
EtOH ethanol
FBS fetal bovine serum
hDAT human dopamine transporter
HEPES 4-(2-hydroxyethyl)-1-piperazineethanesulfonic acid
hNET human norepinephrine transporter
hSERT human serotonin transporter
5-HT 5-hydroxytryptamine
IPA isopropyl alcohol
IPAc isopropyl acetate
MeCN acetonitrile
MeOH methanol
MSA multiple system atrophy
NA noradrenaline
NE norepinephrine
NET norepinephrine transporter
NF National Formulary grade
PAF primary autonomic failure
PBS phosphate buffered saline
PD+ Parkinson's disease plus symptoms of nOH
SBP systolic blood pressure
SERT serotonin transporter
TFA trifluoroacetic acid
THF tetrahydrofuran
Tris tris(hydroxymethyl)aminomethane Other abbreviations used herein but not defined have their ordinary meaning as understood by persons having ordinary skill in the art to which they pertain.

$^1$H NMR spectra were recorded on a 400 MHz Varian AS400 spectrometer, unless otherwise indicated. Chemical shifts are reported as δ values in ppm relative to tetramethylsilane (TMS) as an internal standard. Coupling constants (Jvalues) are given in hertz (Hz) and multiplicities are reported using the following abbreviations: s=singlet, d=doublet, t=triplet, q=quartet, m=multiplet, br=broad, nd=not determined.

Example 1

Preparation of 4-(2-Hydroxymethylphenyl)piperidine-1-carboxylic Acid tert-Butyl Ester 4-(2-Carboxyphenyl)piperidine-1-carboxylic acid t-butyl ester (5.0 g, 16 mmol, 1.0 eq.) and THF (130 mL, 1.7 mol) were combined at room temperature under nitrogen. Borane dimethyl sulfide complex (2.9 mL, 33 mmol, 2.0 eq.) was added dropwise and the mixture was stirred for 5 minutes, then heated at reflux for 1 hour. The mixture was cooled to room temperature and the reaction was quenched by adding MeOH (40 mL) dropwise. The mixture was then concentrated by rotary evaporation and the resulting material was azeotroped with MeOH (2×40 mL). The mixture was then diluted with EtOAc (100 mL), and washed with aqueous hydrochloric acid solution (1 M; 2×50 mL), then aqueous saturated sodium bicarbonate solution (2×50 mL), then saturated aqueous sodium chloride solution (1×50 mL). The organic layer was dried over anhydrous sodium sulfate, filtered, and concentrated in vacuo to yield 4-(2-hydroxymethylphenyl)-piperidine-1-carboxylic acid t-butyl ester (4.8 g) as a clear, light yellow oil that solidified upon sitting.

$^1$H NMR (CDCl$_3$) δ (ppm) 7.34-7.22 (m, 3H); 7.19 (dt, J=1.6 Hz, 7.2, 1H); 4.73 (s, 2H); 4.32-4.14 (m, 2H); 3.00 (tt, J=4.0 Hz, 12.0, 1H); 2.80 (t, J=11.6 Hz, 2H); 1.78-1.56 (m, 4H); 1.47 (m, 9H).

Example 2

Preparation of 4-[2-(Toluene-4-sulfonyloxymethyl) phenyl]piperidine-1-carboxylic Acid tert-Butyl Ester 4-(2-Hydroxymethylphenyl)piperidine-1-carboxylic acid t-butyl ester (0.4 g, 1.0 mmol, 1.0 eq.) and triethylenediamine (220 mg, 2.0 mmol, 1.4 eq.) were dissolved in DCM (11 mL, 170 mmol). The mixture was cooled at 0° C. under nitrogen and p-toluenesulfonyl chloride (290 mg, 1.5 mmol, 1.1 eq.) was added. The resulting mixture was stirred at 0° C. for 60 minutes. The mixture was diluted with EtOAc (50 mL) and washed with water (2×25 mL). The organic layer was dried over anhydrous sodium sulfate, filtered and concentrated by rotary evaporation to yield the title compound (500 mg), which was used without further purification.

$^1$H NMR (CDCl$_3$) δ (ppm) 7.81 (t, J=2.0 Hz, 1H); 7.79 (t, J=2.0 Hz, 1H); 7.37-7.32 (m, 4H); 7.25-7.21 (m, 1H); 7.21-7.13 (m, 1H); 5.12 (s, 2H); 4.34-4.12 (m, 2H); 2.81-2.61 (m, 3H); 2.45 (s, 3H); 1.70-1.52 (m, 4H); 1.48 (s, 9H).

Example 3

Preparation of 4-[2-(2,4,6-Trifluorophenoxymethyl) phenyl]piperidine Trifluroacetic Acid Salt 4-[2-(Toluene-4-sulfonyloxymethyl)phenyl]piperidine-1-carboxylic acid tert-butyl ester (2.1 g, 4.7 mmol, 1.0 eq.) was dissolved in MeCN (46 mL, 890 mmol) and added to potassium carbonate (1.9 g, 14 mmol, 3.0 eq.) and 2,4,6-trifluorophenol (1.0 g, 7.0 mmol, 1.5 eq.). The mixture was shaken at 50° C. overnight, then cooled to room temperature.

The supernatant was separated from the potassium carbonate and other solids. TFA (7 mL, 90 mmol, 20.0 eq.) was added to the supernatant and the mixture was shaken overnight at room temperature. The solution was then concentrated and the residue was dissolved in 1:1 acetic acid/water (5.0 mL). Additional acetic acid (2.0 mL) was added and the mixture was filtered and purified by preparative HPLC to yield the title compound (1.3 g, 97.5% purity). MS m/z: [M+H]$^+$ calcd for C$_{18}$H$_{18}$F$_3$NO, 322.13; found 322.2.

$^1$H NMR (CDCl$_3$) δ (ppm) 9.83 (br.s, 1H); 9.32 (br.s, 1H); 7.46-7.39 (m, 2H); 7.32 (d, J=6.8 Hz, 1H); 7.26-7.21 (m, 1H); 6.76-6.66 (m, 2H); 5.07 (s, 2H); 3.69-3.50 (m, 2H); 3.38 (t, J=11.6 Hz, 1H); 3.20-3.02 (m, 2H); 2.19 (q, J=12.8 Hz, 2H); 2.12-2.01 (m, 2H).

Example 4

Preparation of 4-(2-Hydroxymethylphenyl)piperidine-1-carboxylic Acid tert-Butyl Ester 4-(2-Carboxyphenyl)piperidine-1-carboxylic acid tert-butyl ester (5.0 g, 160 mmol, 1.0 eq.) and THF (100 mL, 1.0 mol) were combined at room temperature under nitrogen. Borane-THF complex in THF (1.0 M, 32.7 mL, 32.7 mmol, 2.0 eq.) was added dropwise over 10 minutes (5° C. exotherm, gas evolution). The reaction mixture was stirred at room temperature for 5 minutes, then heated at 50° C. for 1 hour. The reaction mixture was cooled to room temperature and the reaction was quenched by slowly adding MeOH (30 mL) (mild exotherm, significant gas evolution). The mixture was then concentrated by rotary evaporation. The resulting material was azeotroped with MeOH (2×50 mL). The crude product was dissolved in EtOAc (100 mL) and washed with saturated aqueous sodium bicarbonate solution (50 mL) and then saturated aqueous sodium chloride solution (50 mL). The organic layer was dried over anhydrous sodium sulfate, filtered, and concentrated in vacuo to yield 4-(2-hydroxymethylphenyl)piperidine-1-carboxylic acid tert-butyl ester (4.4 g) as a clear, light yellow oil that solidified upon sitting.

Example 5

Preparation of 4-(2-Methanesulfonyloxymethylphenyl)piperidine-1-carboxylic Acid tert-Butyl Ester 4-(2-Hydroxymethylphenyl)piperidine-1-carboxylic acid tert-butyl ester (50.0 g, 172 mmol, 1.0 eq.) was dissolved in DCM (500 mL, 8000 mmol). The mixture was cooled at 0° C. under nitrogen and methanesulfonic anhydride (44.8 g, 257 mmol, 1.5 eq.) was added in one portion. Diisopropylethylamine (47.8 mL, 274 mmol, 1.6 eq.) was added dropwise over 5 minutes and the mixture was stirred at 0° C. for 90 minutes. Water (400 mL, 20 mol) was added and the mixture was stirred for 5 minutes. The phases were separated, and the organic layer was washed with water (300 mL), dried over anhydrous sodium sulfate, and the solvent removed to yield the title compound (70 g) as a thick oil, which was used without further purification.

$^1$H NMR (400 MHz, DMSO-d$_6$) δ (ppm) 7.37-7.43 (m, 3H), 7.31 (d, 1H), 7.22 (m, 2H), 5.38 (s, 2H), 4.28 (m, 2H), 2.92-3.10 (m, 1H), 2.92 (s, 3H), 2.80-2.92 (m, 2H), 1.63-1.81 (m, 4H), 1.51 (s, 9H).

Example 6

Preparation of 4-[2-(2,4,6-Trifluorophenoxymethyl) phenyl]piperidine-1-carboxylic Acid tert-Butyl Ester 4-(2-Methanesulfonyloxymethylphenyl)piperidine-1-carboxylic acid tert-butyl ester (27.0 g, 60.6 mmol, 1.0 eq.) was dissolved in MeCN (540 mL) and added to potassium carbonate (25 g, 180 mmol, 3.0 eq.) and 2,4,6-trifluorophenol (13.5 g, 90.9 mmol, 1.5 eq.). The mixture was stirred vigorously at 50° C. for 6 hours, removed from the heat, and stirred overnight. The mixture was cooled at room temperature and diluted with EtOAc (700 mL) and water (700 mL). The phases were separated and the organic layer was washed with aqueous sodium hydroxide solution (1.0 M; 2×400 mL) and saturated aqueous sodium chloride solution (1×400 mL), and then dried over anhydrous sodium sulfate. The solvent was then removed to yield crude 4-[2-(2,4,6-trifluorophenoxymethyl)phenyl]piperidine-1-carboxylic acid tert-butyl ester (25.0 g). The crude product was combined with smaller scale runs for a total of 30 g and purified by chromatography (0-10% EtOAc in hexanes) to yield 4-[2-(2,4,6-trifluorophenoxymethyl)phenyl]piperidine-1-carboxylic acid tert-butyl ester (22.0 g).

Example 7

Preparation of 4-[2-(2,4,6-Trifluorophenoxymethyl) phenyl]piperidine Hydrochloride 4-[2-(2,4,6-Trifluorophenoxymethyl)phenyl]piperidine-1-carboxylic acid tert-butyl ester (22.0 g, 31.3 mmol, 1.0 eq.) was combined with 1.25 M HCl in EtOH (250 mL, 310 mmol, 10.0 eq.). The mixture was stirred at room temperature for 8 hours, then stored at −10° C. for approximately 48 hours. Most of solvent was removed by rotary evaporation. To the resulting thick slurry was added EtOAc (80 mL), followed by stirring at room temperature for 2 hours. A first crop of crystals was isolated by filtration, and the filter cake was washed with EtOAc (20 mL) and dried to yield the title compound (8.5 g, >99% purity) as a white solid. HPLC of the filtrate shows ~25% area of product. For the second crop, the solvent was removed by rotary evaporation and the resulting solid (~10 g) was slurried in EtOAc (40 mL), first at room temperature, then at 60° C., and again at room temperature to yield the title compound as a hydrochloride salt (1.7 g, >99% purity).

Two lots of the hydrochloride salt (18.5 g, 51.7 mmol) were combined with EtOAc (75 mL, 770 mmol). The resulting thick but free-flowing slurry was heated at 65° C. for 30 minutes, cooled to room temperature, and filtered. The flask and the filter cake were washed with EtOAc (20 mL), and the solids dried under high vacuum at room temperature overnight to yield the crystalline hydrochloride salt (18.2 g, 99.3% purity).

Example 8

Preparation of 4-[2-(2,4,6-Trifluorophenoxymethyl)phenyl]piperidine Hydrochloride Acetyl chloride (83.5 mL, 1170 mmol) was slowly added to EtOH (140 mL, 2.4 mol). 4-[2-(2,4,6-Trifluorophenoxymethyl)phenyl]piperidine-1-carboxylic acid tert-butyl ester (55.0 g, 117 mmol) dissolved in EtOH (100 mL, 2.0 mol) was added and the resulting mixture was stirred at room temperature for 6 hours. Most of solvent was removed by rotary evaporation. To the resulting thick slurry was added EtOAc (300 mL), followed by partial solvent removal to ~100 mL. EtOAc (200 mL) was added and the resulting slurry was stirred for 1 hour, filtered and dried to yield the title compound (28.0 g, ~99% purity). The filtrate was concentrated to a thick paste and IPAc (100 mL) was added, stirred for 1 hour, filtered and dried to further yield 5.0 g of the hydrochloride salt (~99% purity).

Two lots of the hydrochloride salt (83.0 g, 230 mmol, ~99% purity) were combined with EtOAc (250 mL, 2.6 mol). The resulting slurry was heated at 70° C. and then slowly cooled to room temperature, followed by stirring overnight. The resulting free-flowing slurry was filtered and the filter cake was washed with EtOAc (50 mL) then dried under high vacuum for approximately 48 hours to yield the crystalline hydrochloride salt (81.0 g, >99% purity).

The crystalline hydrochloride salt (50.0 g, 1.40 mol, >99% purity) was dissolved in IPA (250 mL, 3.3 mol), and the resulting slurry was heated to 75° C. Water (25 mL, 1.4 mol) was added. Complete dissolution was observed in 5 minutes, and the internal temperature of the solution was 65° C. The solution was slowly cooled to room temperature and then stirred at room temperature overnight. The resulting solids were filtered and dried under air for 2 hours to yield a semi-dry product. The solids were then dried under high vacuum at room temperature for approximately 48 hours to yield the title crystalline hydrochloride salt (44.1 g, 99.5% purity). This material was used in the PXRD and DSC analyses described in Examples 9 and 10.

Example 9

Powder X-Ray Diffraction

Powder X-ray diffraction patterns were obtained with a Rigaku Miniflex PXRD diffractometer using Cu Ku (30.0 kV, 15.0 mA) radiation. The analysis was performed with the goniometer running in continuous-scan mode of 2° (2θ) per min with a step size of 0.03° over a range of 2 to 400 in two-theta angle. Samples were prepared on quartz specimen holders as a thin layer of powdered material. The instrument was calibrated with a silicon metal standard within +0.02° two-theta angle. The samples were hand ground prior to testing, in order to reduce particle size interferences to the relative intensities. A representative PXRD pattern for the crystalline hydrochloride salt of Example 8 is shown in FIG. 1 of U.S. Pat. No. 8,304,433 B2. The PXRD peaks, in order of descending relative intensity are shown in Table 1. All PXRD peak intensities were corrected by subtracting the corresponding background intensity for each peak.

TABLE 1

Powder X-Ray Diffraction Data

| Intensity % | 2-Theta | Intensity % | 2-Theta |
|---|---|---|---|
| 100 | 17.16 | 30 | 27.24 |
| 66 | 16.06 | 26 | 29.60 |
| 55 | 10.22 | 16 | 4.44 |
| 51 | 26.32 | 24 | 31.94 |
| 43 | 18.38 | 19 | 23.76 |
| 33 | 21.78 | 22 | 8.11 |
| 32 | 13.18 | | |

In one embodiment, the crystalline hydrochloride salt employed in the present invention is characterized by a powder x-ray characterized comprising diffraction peaks at 2θ values of 4.44±0.20, 10.22±0.20, 17.16±0.20 and 21.78±0.20. In another embodiment, the crystalline hydrochloride salt is further characterized by having one or more additional diffraction peaks at 2θ values selected from 8.11±0.20, 13.18±0.20, 16.06±0.20, 18.38±0.20, 23.76±0.20, 26.32±0.20, 27.24±0.20, 29.60±0.20 and 31.94±0.20.

Example 10

Differential Scanning Calorimetry

Differential scanning calorimetry (DSC) was performed using a TA Instruments Model Q-100 module with a Thermal Analyst controller. Data were collected and analyzed using TA Instruments Thermal Solutions software. A 2.8 mg sample of the crystalline hydrochloride salt of Example 8 was accurately weighed into a covered aluminum pan. After a 5 minute isothermal equilibration period at 22° C., the sample was heated using a linear heating ramp of 10° C./min from 22° C. to 250° C. A representative DSC thermograph is shown in FIG. 2 of U.S. Pat. No. 8,304,433 B2. The DSC thermograph demonstrates that the crystalline hydrochloride salt has excellent thermal stability with a melting point at about 196.9° C.

In one embodiment, the crystalline hydrochloride salt employed in the present invention is characterized by a differential scanning calorimetry trace having a melting point of about 197±2° C.

Example 11

Radioligand Binding and Neurotransmitter Uptake Assays

The in vitro pharmacology of 4-[2-(2,4,6-trifluorophenoxymethyl)phenyl]-piperidine at human recombinant and rat native monoamine transporters was characterized as described in Smith et al., *Inter. J. Neuropsychopharmcol.* (2015) 1-11; and Tsuruda et al., *J. Pharmacol. Toxicol. Meth.* (2010) 61:192-204. See also, e.g., U.S. Pat. No. 8,304,432 B2 and U.S. Pat. No. 8,304,433 B2. Radioligands were sourced commercially (Perkin Elmer LifeSciences or GE Healthcare Life Sciences).

Briefly, membranes prepared from HEK293 (Human Embryonic Kidney 293) or CHO-K1 (Chinese Hamster Ovary-K1) cells stably transfected with human recombinant SERT (HEK293-hSERT), NET (HEK293-hNET), or DAT (CHO-KT-hDAT) were incubated for 1 hr at 22° C. in the absence, or presence, of 4-[2-(2,4,6-trifluorophenoxymethyl)phenyl]piperidine and [$^3$H]-citalopram (1.0 nM) for SERT, [$^3$H]-nisoxetine (2.0 nM) for NET, and [$^3$H]-WIN35428 (3.0 nM) for DAT in 50 mM Tris-HCl, 120 mM NaCl, 5 mM KCl, 0.025% BSA, 100 µM ascorbic acid, pH 7.4. Rat cortical membrane preparations were incubated with [$^3$H]-citalopram (2.0 nM) for SERT or [3H]-nisoxetine (4.0 nM) for NET for 1 hr at 22° C. In neurotransmitter uptake assays, HEK293-hSERT, hNET, or hDAT cells, respectively, were pre-incubated for 30 min at 37° C. in the absence, or presence, of 4-[2-(2,4,6-trifluorophenoxymethyl)phenyl]-piperidine in 7.5 mM HEPES, 12.5 mM Tris-HCl, 2.2 mM Na-phosphate, 120 mM NaCl, 5 mM KCl, 0.4 mM MgCl$_2$, 7.5 mM glucose, 1.7 mM CaCl$_2$, 250 µM ascorbic acid, 150 µM pargyline, 0.025% BSA, pH 7.4 prior to incubation with [$^3$H]-5-HT (20 nM), [$^3$H]-NE (40 nM), or [$^3$H]-DA (100 nM) for 10 min. Rat cortical synaptosomes were incubated with [$^3$H]-5-HT or [$^3$H]-NE for 6 min and striatal synaptosomes with [$^3$H]-DA for 6 min. Binding and uptake assays were terminated by rapid filtration and radioactivity determined by liquid scintillation spectroscopy. Final [$^3$H]-neurotransmitter concentrations were significantly below the respective $K_m$ such that pIC$_{50}$ approximated functional pK$_i$. Selectivity for NET (rounded to one significant FIGURE) was determined as follows:

$$\text{Selectivity} = 10^{(pKi \text{ or } pIC50 \text{ at NET minus } pKi \text{ or } pIC50 \text{ at SERT or DAT})}$$

The in vitro pharmacological profile of 4-[2-(2,4,6-trifluorophenoxymethyl)-phenyl]piperidine was similar at human and rodent monoamine transporters as shown in Table 2.

TABLE 2

In Vitro Pharmacology at Human Recombinant and Rat Native SERT, NET, and DAT Transporters

| Species | SERT | NET | DAT |
|---|---|---|---|
| Neurotransmitter Uptake Inhibition: pIC$_{50}$ | | | |
| Human | 8.0 (7.8, 8.2) | 8.6 (8.4, 8.7) | 6.8 (6.6, 6.9) |
| Rat | 7.9 (7.8, 7.9) | 8.9 (8.6, 9.1) | 6.9 (6.8, 6.9) |
| Transporter Binding: pK$_i$ | | | |
| Human | 8.5 (8.5, 8.6) | 8.8 (8.8, 8.9) | 6.7 (6.7, 6.8) |
| Rat | 8.5 (8.3, 8.6) | 8.7 (8.5, 8.9) | N.D. |

Data are expressed as mean pIC$_{50}$ (negative decadic logarithm IC$_{50}$) and p$_K$ (negative decadic logarithm K$_1$) values. Data represents mean (with 95% confidence intervals in parentheses) from 3 to 9 individual experiments. N.D.=not determined.

The data in Table 2 demonstrate that 4-[2-(2,4,6-trifluorophenoxymethyl)phenyl]-piperidine is a potent inhibitor of NET and SERT, but not DAT, with 4-fold higher potency for inhibition of NET over SERT. Similarly, 4-[2-(2,4,6-trifluorophenoxymethyl)phenyl]piperidine is a potent inhibitor of both [$^3$H]-NE and [$^3$H]-5-HT uptake into rat cortical synaptosomes, with an apparent functional selectivity (10-fold) for NET over SERT, similar to that observed at human transporters. Consistent with the functional inhibition studies, 4-[2-(2,4,6-trifluorophenoxymethyl)phenyl]piperidine exhibited a high affinity for binding to human NET and SERT, but not DAT (Table 2). Apparent binding affinity values for rat-native NET and SERT in membranes prepared from rat cortices were similar (overlapping confidence intervals) to the corresponding values at human transporters, consistent with a lack of species dependence (Table 2).

Example 12

Ex Vivo Transporter Occupancy Studies

Adult male Sprague Dawley rats (Charles River) were housed under controlled laboratory conditions (temperature at 21±1° C.) on a 12:12 hour light-dark cycle. Animals were given free access to food and water upon arrival to the facility and animals were acclimatized to their holding room for at least 48 hours. Animals were fasted but allowed free access to water for 15-18 hours prior to dosing.

Rats (n=6/timepoint/dose level) received a single oral dose of 4-[2-(2,4,6-trifluorophenoxymethyl)phenyl]piperidine (0.3, 1, 5, 10, 30, and 60 mg/kg) and were euthanized by decapitation at specified time points (0.5, 2, 4, 6, and 8 hr for 5 mg/kg dose level; 2 hr for 0.3, 1, 10, 30, and 60 mg/kg dose levels) post-administration. Spinal cords were dissected for ex vivo transporter occupancy and PK assessments from the same animals. The spinal cord was harvested by hydraulic extrusion using phosphate-buffered saline, and the lumbar segment dissected and frozen on dry ice. The remaining spinal cord segments were collected and homogenized in water (25% w/w) for PK analysis. All samples were stored at −80° C. until analysis.

A kinetic radioligand binding assay was used to determine NET and SERT occupancy in rat spinal cord, as described previously in Bourdet et al., J. Pharm. Exp. Ther. (2012) 341:137-145. PK/PD parameters were estimated by a compartmental modeling approach (WinNonlin Version 5.0.1, Pharsight Corporation). One- and two-compartment PK models with first-order absorption and elimination were evaluated. The one-compartment model was selected. The pharmacodynamics model was an effect compartment $E_{max}$ model linked directly to the central PK compartment (WinNonlin PK Model 3, PD Model 101). Selection of models was based upon best fit in terms of visual inspection, Akaike Information Criteria, and weighted residual sum of squares using the Gauss-Newton minimization method. The following parameters were estimated:

k01 (hr$^{-1}$): First-order absorption rate constant.

V/F (L/kg): Volume of the central compartment divided by oral bioavailability k10 (hr$^{-1}$): Elimination rate constant from the central compartment $E_{max}$ (% occupancy): Maximal SERT or NET occupancy in spinal cord EC$_{50}$ (ng/mL): Plasma 4-[2-(2,4,6-trifluorophenoxymethyl)phenyl]piperidine concentration associated with 50% SERT or NET occupancy k$_{eo}$ (hr$^{-1}$): First-order equilibration rate constant between the central pharmacokinetic compartment and the pharmacodynamic effect compartment PK and PD parameter estimates derived from the effect compartment PK/PD analysis for NET and SERT occupancy shown in Table 3.

TABLE 3

Pharmacokinetic and Pharmacodynamic Parameter Estimates for 4-[2-(2,4,6-trifluorophenoxymethyl)phenyl]piperidine Norepinephrine and Serotonin Transporter Occupancy in Rat Spinal Cord

| Parameter | SERT | NET |
|---|---|---|
| $E_{max}$ (% occupancy) | 79.0 (53) | 92.0 (19) |
| EC$_{50}$ (ng/mL) | 50.8 (87) | 11.7 (6.8) |
| k$_{eo}$ (hr$^{-1}$) | 11.0 (86) | 1.78 (57) |
| k01 (hr$^{-1}$) | 0.777 (108) | |

TABLE 3-continued

Pharmacokinetic and Pharmacodynamic Parameter Estimates for 4-[2-(2,4,6-trifluorophenoxymethyl)phenyl]piperidine Norepinephrine and Serotonin Transporter Occupancy in Rat Spinal Cord

| Parameter | SERT | NET |
|---|---|---|
| k10 (hr$^{-1}$) | 0.319 (81) | |
| V/F (L/kg) | 54.8 (66) | |

Final parameter estimates are listed with the coefficient of variation (% CV) on each parameter estimate provided in parentheses.

As shown in Table 3, the estimated $EC_{50}$ for occupancy was 11.7 ng/mL for NET and 50.8 ng/mL for SERT in rat spinal cords. Accounting for species differences in plasma protein binding (90.2% and 79.1% in rat and human, respectively), the projected human plasma $EC_{50}$ values were 5.5 ng/mL for NET and 23.9 ng/mL for SERT.

Example 13

Cardiovascular Model in an Anesthetized Rat

These studies were conducted to assess the effect of a single administration of 4-[2-(2,4,6-trifluorophenoxymethyl)phenyl]piperidine on heart rate (HR) and mean arterial pressure (MAP) in anesthetized rats. Using this cardiovascular model, the intrinsic effect on HR and the inhibition of tyramine pressor response were evaluated as surrogate measures that reflect the ability of 4-[2-(2,4,6-trifluorophenoxymethyl)phenyl]piperidine to inhibit norepinephrine transporters in the periphery.

A. Experimental Design

Normotensive male Sprague-Dawley rats weighing between 250-350 g were anesthetized with an intraperitoneal injection (IP) of thiobutabarbital (Inactin). All animals were kept under complete anesthesia (i.e., absence of response to toe pinch test) for the surgery and for the duration of the study. The right common carotid artery and jugular vein were isolated and catheterized. The trachea was intubated to keep the airway open during the study. After completion of surgery, the arterial catheter was connected to a pressure transducer and baseline blood pressure [Systolic (SBP), Mean Arterial (MAP) and Diastolic (DBP)] and heart rate (HR) were recorded using the Notocord-HEM data acquisition system. Following at least 60 min of baseline (i.e., the last 10 min was stable), vehicle (10% Tween20, 2 mL/kg, IP) was administered and any potential effect was monitored for at least 10 min. After this period, rats were injected with either vehicle or 4-[2-(2,4,6-trifluorophenoxymethyl)phenyl]piperidine (0.01-30 mg/mL, 2 mL/kg, IP) and changes in MAP and HR were monitored for 25 min. Rats were then challenged intravenously via the jugular vein catheter, with non-cumulative bolus doses of tyramine (0.03, 0.1, 0.3, and 1 mg/kg, 1 mL/kg, IV) given at 5 min intervals. After the last dose of tyramine, data acquisition continued for another 10 min before the experiment was terminated. In a separate group of animals, blood was collected to assess the concentration of 4-[2-(2,4,6-trifluorophenoxymethyl)phenyl]piperidine in plasma at 15 min and 60 min after dosing. Free plasma concentrations obtained from 15 min were used to construct the concentration response curve (CRC) to MAP and HR while concentrations from 60 min were used for the tyramine CRC. Animals were euthanized by carbon dioxide asphyxiation followed by thoracotomy.

B. Data Analysis

Intrinsic hemodynamic effects were reported as the maximum change in MAP or HR induced by 4-[2-(2,4,6-trifluorophenoxymethyl)phenyl]piperidine before tyramine challenge. Inhibition of tyramine effect was normalized to the response to 1 mg/kg dose of tyramine in the vehicle control group. Concentration response curves (CRCs) of the change in MAP, HR and inhibition of tyramine response were analyzed through iterative curve fitting to a logistic equation using Prism 5.00™ (GraphPad, Inc.). The equation used was as follows:

$$Y=(Bottom+Top-Bottom)/(1+10^{\wedge}((Log\ EC_{50}-X)*HillSlope))$$

where X is the logarithm of dose, Y is the response, Y starts at Bottom (constrained to 0 for all) and goes to Top with a sigmoid shape. When change in MAP or HR was reduced at the higher dose(s), a more accurate estimate of Top (i.e., maximum efficacy) was obtained by carrying over the maximum effect which occurred at a lower dose to all the subsequent higher doses. For the tyramine CRC, the TOP was constrained to 100.

Potency of the pressor effect was reported as MAP $PC_{10}$ which is the free plasma concentration that produced a change in MAP of 10 mm Hg and the potency of the HR effect was reported as HR $PC_{25}$ which is the free plasma concentration that produced a change in HR of 25 bpm. Lastly, the potency to inhibit the tyramine effect was reported as Tyr $EC_{50}$ which is the concentration that produced 50% inhibition of tyramine-induced (1 mg/kg, IV) increase in SBP.

Inhibitory potencies ($pIC_{50}$ values) obtained from measuring the inhibition of labelled 5-HT uptake by rat serotonin transporters (rSERT) in rat cortical synaptosomes were converted to $IC_{50}$ values using this formula:

$$Y=(10^{\wedge}(-x))x(10^{\wedge}9)$$

C. Results

4-[2-(2,4,6-Trifluorophenoxymethyl)phenyl]piperidine (0.01-30 mg/kg, IP) dose dependently increased MAP and HR in anesthetized rats. When plotted against the corresponding free plasma concentration for each dose, the estimated MAP and HR potencies were 101.4 nM (MAP $EC_{10}$) and 8.6 nM (HR $EC_{25}$). The maximum changes in MAP and HR were 13.2 (4.4-22.1) mm Hg and 28.1 (22.4-33.7) bpm, respectively. 4-[2-(2,4,6-Trifluorophenoxymethyl)phenyl]piperidine also inhibited tyramine-induced increases in SBP. When expressed as % inhibition of response to 1 mg/kg of intravenously administered tyramine, the estimated potency of 4-[2-(2,4,6-trifluorophenoxymethyl)phenyl]piperidine was 0.86 nM.

D. Conclusion

In a cardiovascular model in anesthetized rat, 4-[2-(2,4,6-trifluorophenoxymethyl)-phenyl]piperidine exhibited potent inhibition of tyramine pressor response and tachycardia which is consistent with inhibition of NET in the periphery.

Example 14

Preparation of Oral Dosing Solutions

Oral dosing solutions of 4-[2-(2,4,6-trifluorophenoxymethyl)phenyl]piperidine hydrochloride were prepared in two steps. First, a 3 mg/mL aqueous stock solution was prepared and then, oral solutions in filtered apple juice having different dose strengths were prepared prior to dosing.

A. Preparation of Stock Solution

4-[2-(2,4,6-Trifluorophenoxymethyl)phenyl]piperidine hydrochloride (500 mg, 89.9% purity) was added to a 250 mL clear glass bottle. Sterile Water for Injection (150 mL) was added and the bottle was capped. The bottle was gently swirled in a circular motion until no solid material was observed (about 20 minutes). If needed, the bottle can also be sonicated. The bottle was labeled and the stock solution (3 mg/mL) was used within 2 hours or stored in a refrigerator at 2-8° C. until use. Any stock solution not used within 6 days of initial preparation was discarded.

B. Preparation of Oral Dosing Solutions

Oral dosing solutions having seven different dose strengths were prepared for use in either Part A or Part B of the clinical studies. The dose strengths prepared and the amounts used to prepare each dose strength were as shown in Tables 4 and 5:

TABLE 4

Oral Dosing Solutions (Part A)

| Dose (mg) | Final Conc. (µg/mL) | Stock Vol. (mL) | Apple Juice Vol. (mL) | Oral Solution Prepared (mL) | Final Dosing Vol. (mL) |
|---|---|---|---|---|---|
| 1 | 100 | 1 | 29 | 30 | 10 |
| 2.5 | 250 | 2 | 22 | 24 | 10 |
| 5 | 500 | 4 | 20 | 24 | 10 |
| 10 | 1000 | 10 | 20 | 30 | 10 |

TABLE 5

Oral Dosing Solutions (Part B)

| Dose (mg) | Final Conc. (µg/mL) | Stock Vol. (mL) | Apple Juice Vol. (mL) | Oral Solution Prepared (mL) | Final Dosing Vol. (mL) |
|---|---|---|---|---|---|
| 1 | 100 | 1 | 29 | 30 | 10 |
| 3 | 300 | 3 | 27 | 30 | 10 |
| 7 | 700 | 7 | 23 | 30 | 10 |
| 15 | 1500 | 15 | 15 | 30 | 10 |

To prepare the oral dosing solutions, the stock solution (3 mg/mL) was removed from the refrigerator and visually checked for any precipitation. If precipitation was present, the stock solution was re-prepared.

Apple juice (at least 40 mL, Mott's 100% Original Apple Juice) was drawn into a 50 mL syringe and a syringe filter (25 mm PVDF Syringe Filter, 0.2 µm, Pall Life Sciences) was attached to the syringe. The apple juice was filtered through the syringe filter with the first 3 mL being discarded and the remaining apple juice being collected in a 125 mL amber bottle.

The amount of stock solution (3 mg/mL) shown in Table 4 or 5 (Stock Volume) was then added to a new 125 mL amber bottle and the corresponding amount of filtered apple juice shown in Table 4 or 5 (Apple Juice Volume) was added to the bottle. The bottle was capped and the contents were mixed by swirling in a circular motion for more than 2 minutes. The resulting solution was stored at ambient room temperature for up to 18 hours before dosing the patient. Prior to dosing the patient, a 10 mL aliquot of the oral solution was transferred into a new 125 mL amber bottle.

Example 15

Preparation of Oral Dosing Tablets

Microcrystalline cellulose (4.476 kg; AVICEL Microcrystalline Cellulose, NF, Ph. Eur Type PH-112) and anhydrous lactose (2.450 kg; anhydrous 60M NF, EP) were loaded into a blending bin and blended for 5 minutes at 20 rpm. The resulting mixture was transferred into a double PE-lined container ("Premix 1") and separated into two parts, one part weighing about 1 kg ("Premix 1A) and the other part comprising the remainder ("Premix 1B"). About one-half of Premix 1A was added to a bin followed by 4-[2-(2,4,6-trifluorophenoxymethyl)phenyl]piperidine hydrochloride (38.93 g; milled), and then the second half of Premix 1A was added. The resulting mixture was blended for 10 minutes at 20 rpm and then transferred into a double PE-lined container ("Active Premix 2"). About one-half of Premix 1B was passed through a mill fitted with a 1.0 mm screen at 1000 rpm (800-1200 rpm), impact forward, followed by Active Premix 2 and then the second half of Premix 1B. The milled materials were collected into a double PE-lined container ("Milled Premix 3"). Milled Premix 3 was passed through a 40-mesh hand screen, and the sifted material was transferred into a blending bin and blended for 10 minutes at 20 rpm ("Active Blend"). One full scoop of Active Blend was removed and mixed manually with magnesium stearate (35.0 g, NF) in a polyethylene bag. This mixture was then passed through a 40-mesh hand screen. The screened mixture was then added back into the blending bin and the entire mixture was blended for 5 minutes at 20 rpm ("Final Blend"). The Final Blend was compressed into 200 mg tablets using a tablet press and the tablets were passed through a deduster and metal detector. The acceptable tablets were collected into double PE-lined containers.

Purified water (1.587 kg, USP) was added into a clean stainless steel solution preparation vessel and the mixer speed was adjusted to form a vortex. A polyvinyl alcohol-based film coating (280.0 g; OPADRY II Pink 85G64744, Colorcon, Inc., West Point, Pa.) was added into the vortex in the mixing tank and the mixing speed was reduced so there was no longer a vortex and mixing was continued for at least 45 minutes or until the color was uniformly dispersed by visual observation. Gentle mixing was maintained before and during the coating process. The tablets prepared above were loaded into a coating pan and the pan speed was set at 10 rpm. The coating solution was pumped into the coating pan. The coating solution weight change was monitored as it was pumped into the coating pan and addition of the coating solution was stopped when a 4% tablet dried weight gain was achieved based on coating suspension usage. The resulting pink tablets contained about 1 mg of 4-[2-(2,4,6-trifluorophenoxymethyl)-phenyl]piperidine (free base equivalents).

Yellow tablets containing about 5 mg of 4-[2-(2,4,6-trifluorophenoxymethyl)-phenyl]piperidine (free base equivalents) were also prepared using a similar procedure and the following amounts of materials: microcrystalline cellulose (4.320 kg); anhydrous lactose (2.450 kg); 4-[2-(2,4,6-trifluorophenoxymethyl)phenyl]piperidine hydrochloride (194.7 g); magnesium stearate (35.0 g); purified water (1.587 kg); and a polyvinyl alcohol-based film coating (280.0 g; OPADRY II Yellow 85G620027).

Example 16

Clinical Study in Subjects with nOH

A Phase 2 clinical trial study is being conducted with 4-[2-(2,4,6-trifluorophenoxymethyl)phenyl]piperidine hydrochloride ("Study Compound"). The study is a multi-center, randomized, two-part, single-(Part A) and double-blind (Part B) study of the Study Compound versus placebo in subjects with nOH. An open-label, extension study to evaluate efficacy, safety and tolerability of the Study Compound will also be conducted (Part C). Part A follows a daily, single, escalating dose design starting with placebo on Day 1, followed by a dose of 1 mg of Study Compound on Day 2, and proceeding to escalating higher doses of Study Compound on a daily basis up to a maximum dose of 10 mg based on safety, tolerability, and determination of a pressor effect. Part B follows a randomized, placebo-controlled, parallel design evaluating a dose that was determined to be generally well tolerated and to have a pressor effect for a given subject from Part A. Part C is an open-label, extension study to evaluate efficacy (chronic pressor response, symptoms of nOH), safety, and tolerability of Study Compound administered once daily for up to 20 weeks in subjects who were confirmed responders in Part A.

Subjects included in the study are male or female between the age of 40 and 80 years (inclusive) that have been diagnosed with symptomatic orthostatic hypotension due to pure autonomic failure, multiple system atrophy or Parkinson's disease (i.e., PD plus symptoms). At screening, autonomic function testing is conducted to confirm the diagnosis of autonomic dysfunction including sinus arrhythmia and the Valsalva maneuver. Subjects must: (1) demonstrate a ≥30 mm Hg drop in SBP within 5 minutes of standing; (2) demonstrate impaired autonomic reflexes as determined by absence of BP overshoot during phase IV of the Valsalva maneuver; (3) experience dizziness, light-headedness, or fainting when standing; and (4) have an absence of other identifiable causes of autonomic neuropathy.

A. Dose Escalation Study (Part A)

In Part A, all doses (Study Compound and placebo) are administered in a single-blind manner (i.e., subject remains blinded) using an oral dosing solution. Up to 30 subjects are enrolled in Part A. Two days before the start of Part A, subjects are admitted to the clinical research center (CRC) where they remain during the entire dose escalation period. On Day 1, subjects receive a single dose of placebo. On Day 2, subjects receive a single 1 mg dose of Study Compound. On each subsequent day, subjects receive a single escalating dose of Study Compound as follows: 2.5 mg on Day 3; 5 mg on Day 4; 10 mg on Day 5 unless the following preset stopping criteria occur:
- (a) a determination from the Investigator (in collaboration with the Sponsor) that administration of the subsequent next dose may pose a safety concern;
- (b) SBP ≥180 mm or DBP ≥110 mm in the sitting position replicated 2 more times over an hour;
- (c) intolerable side effects as determined by the Investigator; or
- (d) subject receives maximum dose of study medication specified by the protocol.

Once the subject meets any of the above criteria, no further dose escalation is performed. Following a post-dosing observation day in the clinic, the subject is released from the CRC.

Subjects who do not demonstrate a clinically meaningful increase in SBP based on Investigator determination (in collaboration with the Sponsor), or who discontinue study drug prior to reaching the stopping criteria, do not continue to study Part B. Subjects are not required to complete all four Study Compound doses to continue to Study Part B. All subjects who receive at least one Study Compound dose that produces an effective increase in seated BP and is considered to be generally well tolerated are eligible to participate in study Part B and/or Part C.

B. Washout Period

After completion of Part A, subjects undergo a washout period (minimum 8 days not to exceed 36 days). On a daily basis during the first 72 hours from discharge, and then at least weekly during the remainder of the washout period, the Investigator or designee contacts the subject by telephone to review the subject's health status. Any adverse events reported by phone are recorded and followed as medically appropriate as determined by the Investigator. Under the direction of the Investigator, subjects manage their nOH symptoms during the washout period using other medications as prescribed.

C. Randomized, Double-blind, Parallel Design Study (Part B)

Following the washout period, subjects may return to the CRC two days before the start of Part B and are randomized to receive a single dose of either placebo or Study Compound. Treatment assignment in Part B is double blind, with Study Compound prepared as an oral solution by a designated unblinded pharmacist at the CRC. In Part B, in collaboration between the Investigator and the Sponsor, subjects receive a Study Compound dose that achieves a comparable peak exposure relative to the dose determined during Part A to produce an effective increase in seated BP and considered to be generally well tolerated. The individualized dose selected for Part B is determined using pharmacokinetic modeling to achieve comparable exposures to Study Compound corresponding to the final dose administered in Part A as shown in Table 6.

TABLE 6

| Dose Determination for Part B | |
|---|---|
| Final Dose in Part A | Dose for Part B |
| 1 mg | 1 mg |
| 2.5 mg | 3 mg |
| 5 mg | 7 mg |
| 10 mg | 15 mg |

D. Open-Label, Extension Study (Part C)

For Part C, the Study Compound is provided as 1 mg or 5 mg tablets packaged in open-labeled 40-count high density polyethylene bottles. On Day 1, the patient receives a dose equal to the highest dose tolerated during Part A. On Day 2 and thereafter, the patient receive a dose equal to 50% of the dose administered on Day 1 of Part C (rounded up to the nearest 1 mg). For example, if the highest dose in Part A was 10 mg/day, then on Day 1 of Part C, the patient receives 10 mg and on Day 2 and thereafter, the patient receives 5 mg/day. Similarly, if the highest dose in Part A was 5 mg/day, then on Day 1 of Part C, the patient receives 5 mg and on Day 2 and thereafter, the patient receives 3 mg/day. If a patient develops the presence or worsening of previously-observed supine hypertension (SBP ≥180 mm Hg or DBP ≥110 mm Hg) or other adverse events suggesting intolerability, the dose is withheld for 3 days and resumed at a dose level 50% (rounded up to the nearest 1 mg) of the prior dose level. If supine hypertension or other adverse events persists after the dose has been reduced, dosing in that patient is discontinued and appropriate alternative therapy and care provided to the patient as determined by the principal investigator. Additionally, if dose reduction occurs while patient is at home, the patient is brought in for a clinic visit within 2 weeks of the dose reduction.

E. Study Evaluations

1. Efficacy Assessments

Seated and standing systolic blood pressure and completion of an Orthostatic Hypotension Symptom Assessment (OHSA) questionnaire are used to assess efficacy. For Part C, ambulatory blood pressure monitoring is used if available to measure blood pressure every 2 hours for 24-hour period before dosing on Day 1; and 72 to 48 hours before Day 15, Day 29, Day 85 and Day 169 clinic visits. Additionally, blood pressure is taken 20-30 mins before eating each morning about being supine (30 degree elevation) for at least 10 mins.

2. Safety Assessments

Adverse events, clinical laboratory tests (including hematology, serum chemistry, and urinalysis), vital signs, 12-lead ECGs, use of concomitant medications, and physical examinations are used to assess safety.

3. Pharmacokinetic (PK) Assessments

In Part A, blood samples for assessment of Study Compound plasma concentration are taken before dosing (within 30 minutes before the dose and immediately following assessment of standing BP and orthostatic evaluation) and again between 6 and 8 hours post dose immediately following assessment of standing BP and orthostatic evaluation on dosing Days 3 (2.5 mg) and 4 (5 mg). One additional PK sample is taken at 24 hours post dose following the last administered dose after the subject has reached the stopping criteria or at the end of the dose escalation sequence.

In Part B, blood samples for PK are taken before dosing (within 30 minutes before the dose), between 6 and 8 hours post dosing (single time point) and 24 hours post dosing. All PK samples are collected following assessment of BP and orthostatic evaluation as appropriate. The actual collection time is recorded for each blood collection.

In Part C, blood samples are collected 30 minutes prior to dosing on Day 1 and Day 2 and again between 6 and 9 hours post dose on Day 1. Blood samples are also collected when the patient comes into the clinic.

4. Pharmacodynamic (PD) Assessments

In Part A, blood samples for analysis of NE and dihydroxyphenylglycol (DHPG) are collected on dosing Days 1 (placebo), 3 (2.5 mg) and 4 (5 mg) at the time points including twice before dosing (within 30 minutes before the dose and immediately following each assessment of supine and standing BP and orthostatic evaluations) and once again between 6 and 8 hours post dose (immediately following assessment of standing BP and orthostatic evaluations). Two additional PD samples are taken at 24 hours post dose (supine and standing) following the last administered dose after the subject has reached the stopping criteria or at the end of the dose escalation sequence.

In Part B, blood samples for analysis of NE and DHPG are collected on dosing Day 1 at the time points including twice before dosing (within 30 minutes before the dose and immediately following each assessment of supine and standing BP and orthostatic evaluations) and once again between 6 and 8 hours post dose (immediately following assessment of standing BP and orthostatic evaluations).

In Part C, blood samples are collected 30 minutes prior to dosing on Day 1 and Day 2 and again between 6 and 9 hours post dose on Day 1. Blood samples are also collected when the patient comes into the clinic.

F. Study Endpoints

For both Parts A and B, the primary study endpoint is the difference from placebo of seated systolic blood pressure at 6 to 8 hours after drug administration. For Part A, placebo refers to the Day 1 visit, and the difference from placebo refers to the time-matched difference from each Study Compound dosing day (Days 2 through 5) relative to placebo dosing (Day 1). For Part C, primary study endpoint is improvement in the Likert scale for "dizziness, lightheadedness, feeling faint, or feeling like you might black out" (OHSA question 1) at week 4.

The secondary endpoints include: change from placebo in standing SBP at 6 to 8 hours post dose; improvement in the Likert scale for "dizziness, lightheadedness, feeling faint, or feeling like you might black out" (patient's rating of symptoms on average for week prior to question); other questionnaire scores; increase in standing SBP (area under the curve measure at 1, 3, 5 and 10 min while standing); increase in seated SBP (area under the curve for 10 hours following drug administration); and duration of standing during the orthostatic standing test.

Preliminary results of Part A are shown in Table 7. In Table 7, a check mark (✓) indicates that a dose-related improvement was observed when the patient was administered 4-[2-(2,4,6-trifluorophenoxymethyl)phenyl]piperidine hydrochloride relative to placebo. All patients in Table 7 received a maximum dose in Part A of 10 mg/day, except Patient No. 5 who received a maximum dose in Part A of 5 mg/day.

TABLE 7

Preliminary Results of Study - Part A

| Patient No. | Diagnosed Condition[1] | Improvement in Seated SBP | Improvement in Time Standing | Improvement in Dizziness or Lightheadedness |
|---|---|---|---|---|
| 1 | PD+ | ✓[2] | ✓ | |
| 2 | MSA | ✓ | ✓ | |
| 3 | MSA | | | ✓ |
| 4 | MSA | ✓ | ✓ | ✓ |
| 5 | MSA | ✓ | ✓ | ✓ |
| 6 | PAF | | | |
| 7 | PD+ | | | |
| 8 | MSA | ✓ | ✓ | |
| 9 | PAF | ✓ | ✓ | ✓ |
| 10 | PD+ | | ✓ | |
| 11 | PAF | | ✓ | ✓ |
| 12 | MSA | ✓ | | |

[1]MSA = multiple system atrophy
PAF = pure autonomic failure
PD+ = Parkinson's disease plus symptoms of nOH
[2]✓ = Dose-related improvement observed relative to placebo.

The data in Table 7 demonstrate that, of the patients completing Part A, 10 of 12 patients (83%) showed an improvement relative to placebo in at least one of the following: (a) seated systolic blood pressure; (b) standing time; or (c) dizziness or lightheadedness. Four patients (not shown in Table 7) discontinued Part A or were not fully evaluated, due to preexisting supine hypertension (3 patients) or atrial fibrillation (1 patient). Of the MSA patients completing Part A, 6 of 6 patients (100%) showed improvement relative to placebo in at least one category in Table 7.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A method for treating neurogenic orthostatic hypotension and the symptoms thereof in a human patient, the method comprising administering to the patient a compound of formula I:

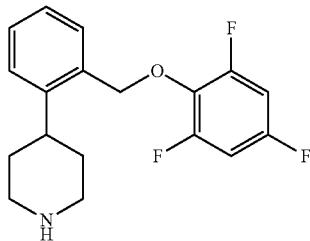

or a pharmaceutically-acceptable salt thereof; wherein the patient has multiple system atrophy, pure autonomic failure, or Parkinson's disease.

2. The method of claim 1, wherein administration of the compound to the patient results in one or more of: (a) an increase in the patient's seated systolic blood pressure; (b) an increase in the patient's standing time; and (c) a decrease in dizziness or lightheadedness experienced by the patient.

3. The method of claim 2, wherein administration of the compound to the patient increases the patient's seated systolic blood pressure.

4. The method of claim 2, wherein administration of the compound to the patient increases the patient's standing time.

5. The method of claim 2, wherein administration of the compound to the patient decreases dizziness or lightheadedness experienced by the patient.

6. The method of claim 1 or 2, wherein the compound is 4-[2-(2,4,6-trifluorophenoxymethyl)phenyl]piperidine hydrochloride.

7. The method of claim 1 or 2, wherein the compound is a crystalline hydrochloride salt of 4-[2-(2,4,6-trifluorophenoxymethyl)phenyl]piperidine characterized by a powder x-ray diffraction pattern comprising diffraction peaks at 2θ values of 4.44±0.20, 10.22±0.20, 17.16±0.20 and 21.78±0.20.

8. The method of claim 7, wherein the crystalline hydrochloride salt of 4-[2-(2,4,6-trifluorophenoxymethyl)phenyl]piperidine is further characterized by having one or more additional diffraction peaks at 2θ values selected from 8.11±0.20, 13.18±0.20, 16.06±0.20, 18.38±0.20, 23.76±0.20, 26.32±0.20, 27.24±0.20, 29.60±0.20 and 31.94±0.20.

9. The method of claim 1 or 2, wherein the compound is a crystalline hydrochloride salt of 4-[2-(2,4,6-trifluorophenoxymethyl)phenyl]piperidine characterized by a differential scanning calorimetry trace having a melting point of about 197±2° C.

10. The method of claim 1 or 2, wherein the patient has multiple system atrophy.

11. The method of claim 1 or 2, wherein the compound is administered in an amount ranging from about 0.5 mg/day to about 20 mg/day.

12. The method of claim 1 or 2, wherein the compound is administered in an amount ranging from about 1 mg/day to about 10 mg/day.

13. A method for treating neurogenic orthostatic hypotension and the symptoms thereof in a human patient, the method comprising administering to the patient a pharmaceutical composition comprising a pharmaceutically-acceptable carrier and a compound of formula I:

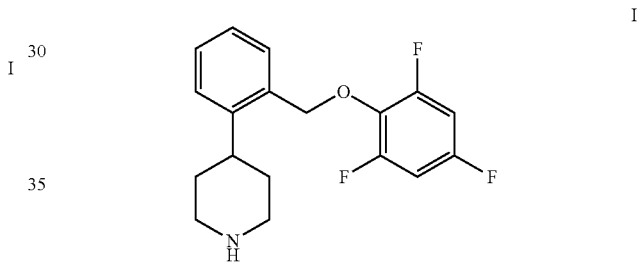

or a pharmaceutically-acceptable salt thereof; wherein the patient has multiple system atrophy, pure autonomic failure, or Parkinson's disease.

14. The method of claim 13, wherein administration of the pharmaceutical composition results in one or more of: (a) an increase in the patient's seated systolic blood pressure; (b) an increase in the patient's standing time; and (c) a decrease in dizziness or lightheadedness experienced by the patient.

15. The method of claim 14, wherein administration of the composition to the patient increases the patient's seated systolic blood pressure.

16. The method of claim 14, wherein administration of the composition to the patient increases the patient's standing time.

17. The method of claim 14, wherein administration of the composition to the patient decreases dizziness or lightheadedness experienced by the patient.

18. The method of claim 13 or 14, wherein the compound is 4-[2-(2,4,6-trifluorophenoxymethyl)phenyl]piperidine hydrochloride.

19. The method of claim 13 or 14, wherein the compound is a crystalline hydrochloride salt of 4-[2-(2,4,6-trifluorophenoxymethyl)phenyl]piperidine characterized by a powder x-ray diffraction pattern comprising diffraction peaks at 2θ values of 4.44±0.20, 10.22±0.20, 17.16±0.20 and 21.78±0.20.

20. The method of claim 19, wherein the crystalline hydrochloride salt of 4-[2-(2,4,6-trifluorophenoxymethyl)

phenyl]piperidine is further characterized by having one or more additional diffraction peaks at 2θ values selected from 8.11±0.20, 13.18±0.20, 16.06±0.20, 18.38±0.20, 23.76±0.20, 26.32±0.20, 27.24±0.20, 29.60±0.20 and 31.94±0.20.

21. The method of claim 13 or 14, wherein the compound is a crystalline hydrochloride salt of 4-[2-(2,4,6-trifluorophenoxymethyl)phenyl]piperidine characterized by a differential scanning calorimetry trace having a melting point of about 197±2° C.

22. The method of claim 13 or 14, wherein the patient has multiple system atrophy.

23. The method of claim 13 or 14, wherein the composition is administered in an amount sufficient to provide about 0.5 mg/day to about 20 mg/day of the compound.

24. The method of claim 13 or 14, wherein the composition is administered in an amount sufficient to provide about 1 mg/day to about 10 mg/day of the compound.

* * * * *

UNITED STATES PATENT AND TRADEMARK OFFICE
CERTIFICATE OF CORRECTION

PATENT NO. : 10,238,642 B2
APPLICATION NO. : 15/685119
DATED : March 26, 2019
INVENTOR(S) : Sharathchandra S. Hegde It is certified that error appears in the above-identified patent and that said Letters Patent is hereby corrected as shown below:

In the Claims

At Column 34, Line 4, Claim 8:
"20" should be "2θ".

Signed and Sealed this
Thirteenth Day of August, 2019

Andrei Iancu
*Director of the United States Patent and Trademark Office*